(12) United States Patent
Han et al.

(10) Patent No.: US 8,440,063 B2
(45) Date of Patent: *May 14, 2013

(54) ELECTROKINETIC CONCENTRATION DEVICES

(75) Inventors: Jongyoon Han, Bedford, MA (US); Sung Jae Kim, Melrose, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 871 days.

This patent is subject to a terminal disclaimer.

(21) Appl. No.: 12/409,447

(22) Filed: Mar. 23, 2009

(65) Prior Publication Data
US 2009/0242406 A1 Oct. 1, 2009

Related U.S. Application Data

(60) Provisional application No. 61/064,784, filed on Mar. 26, 2008.

(51) Int. Cl.
*G01N 27/26* (2006.01)
(52) U.S. Cl.
USPC .................................... 204/630; 204/638
(58) Field of Classification Search ........... 204/630–647
See application file for complete search history.

(56) References Cited

U.S. PATENT DOCUMENTS

| 6,418,968 | B1 | 7/2002 | Pezzuto et al. |
| 7,651,600 | B2 * | 1/2010 | Han et al. ............... 204/601 |
| 2005/0061745 | A1 | 3/2005 | Xie et al. |
| 2005/0284762 | A1 * | 12/2005 | Astorga-Wells et al. ..... 204/451 |
| 2006/0008382 | A1 | 1/2006 | Salamitou et al. |
| 2006/0180469 | A1 * | 8/2006 | Han et al. ............... 204/601 |

OTHER PUBLICATIONS

Wang et al., "Efficient Biomolecule Pre-concentration by Nanofilter-triggered Electrokinetic Trapping", 9th International Conference on Miniaturized Systems for Chemistry and Life Sciences, Oct. 9-13, 2005, pp. 238-240.
Lee et al., "Multiplexed Proteomic Sample Preconcentration Device Using Surface-Patterned Ion-Selective Membrane", Lab Chip, vol. 8, No. 4, pp. 596-601, 2008, no month.
International Search Report and Written Opinion issued in connection with PCT Application No. PCT/US09/37993, issued on Jun. 4, 2009.

* cited by examiner

*Primary Examiner* — Arun S Phasge
(74) *Attorney, Agent, or Firm* — Gesmer Updegrove LLP

(57) ABSTRACT

The present invention provides a device and methods of use thereof in concentrating a species of interest and/or controlling liquid flow in a device. The methods make use of a device comprising a fluidic chip comprising a planar array of channels through which a liquid comprising a species of interest can be made to pass with at least one rigid substrate connected thereto such that at least a portion of a surface of the substrate bounds the channels, and a high aspect ratio ion-selective membrane is embedded within the chip, attached to at least a portion of the channels. The device comprises a unit to induce an electric field in the channel and a unit to induce an electrokinetic or pressure driven flow in the channel.

23 Claims, 11 Drawing Sheets

PDMS Microchannels

Mechanical Cutting
Across Microchannels

PDMS Microchannels

Mechanical Cutting
Across Microchannels

Bend and Drop a Nafion
Droplet on the Edge

Cure at 95°C and Remove Nafion
Residual on PDMS Surface

Plasma Bonding

*t*=2.0sec  *t*=1.0sec  *t*=0.0sec

US 8,440,063 B2

ELECTROKINETIC CONCENTRATION DEVICES

CROSS REFERENCE TO RELATED APPLICATIONS

This application claims the benefit of U.S. Ser. No. 61/064,784, filed on 26 Mar. 2008 which is incorporated in their entirety herein by reference.

GOVERNMENT INTEREST STATEMENT

This invention was made in whole or in part with government support under EB005743 awarded by the National Institutes of Health and under CA119402 awarded by the National Institutes of Health. The government has certain rights in the invention.

FIELD OF THE INVENTION

This invention provides devices and methods of use thereof in concentrating a charged species of interest in solution. This invention provides a concentration device, which is based on electrokinetic trapping of a charged species of interest, which can be further isolated and analyzed.

BACKGROUND OF THE INVENTION

One of the major challenges of proteomics is the sheer complexity of biomolecule samples, such as blood serum or cell extract. Typical blood samples could contain more than 10,000 different protein species, with concentrations varying over 9 orders of magnitude. Such diversity of proteins, as well as their huge concentration ranges, poses a formidable challenge for sample preparation in proteomics.

Conventional protein analysis techniques, based on multidimensional separation steps and mass spectrometry (MS), fall short because of the limited separation peak capacity (up to ~3000) and dynamic range of detection (~$10^4$). Microfluidic biomolecule analysis systems (so-called μTAS) hold promise for automated biomolecule processing. Various biomolecule separation and purification steps, as well as chemical reaction and amplification have been miniaturized on a microchip, demonstrating orders of magnitude faster sample separation and processing. In addition, microfluidic integration of two different separation steps into a multidimensional separation device has been demonstrated. However, most microfluidic separation and sample processing devices suffers from the critical issue of sample volume mismatch. Microfluidic devices are very efficient in handling and processing 1 pL~1 nL of sample fluids, but most biomolecule samples are available or handled in a liquid volume larger than 1 μL. Therefore, microchip-based separation techniques often analyze only a small fraction of available samples, which significantly limits the overall detection sensitivity. In proteomics, this problem is exacerbated by the fact that information-rich signaling molecules (cytokines and biomarkers, e.g.) are present only in trace concentrations (nM~pM range), and there is no signal amplification technique such as polymerase chain reaction (PCR) for proteins and peptides.

What is needed is an efficient sample concentrator, which can take typical sample volume of microliters or more and concentrate molecules into a smaller volume so that it can be separated and detected much more sensitively. Several strategies are currently available to provide sample preconcentration in liquid, including field-amplified sample stacking (FAS), isotachophoresis (ITP), electrokinetic trapping, micellar electrokinetic sweeping, chromatographic preconcentration, and membrane preconcentration. Many of these techniques are originally developed for capillary electrophoresis, and require special buffer arrangements and/or reagents. Efficiency of chromatographic and filtration-based preconcentration techniques depends on the hydrophobicity and the size of the target molecules.

Electrokinetic trapping is another means for such charged biomolecule concentration. When applying an electric field across an ion-selective membrane, a charge-depletion region is developed, which in combination with tangential flow (either pressure-driven or electroosmosis-driven), can concentrate the charged analytes inside a channel. Currently, however, the fabrication of such devices is cumbersome and complex, since the integration of sufficiently thin (~5 um) ion-selective membranes into the device has been challenging. Thin Nafion membranes are easily breakable and handling requires extreme care since the membrane can be easily wrapped around itself, confounding planar device fabrication methods.

Another attempt at planar devices sandwiched a thin ion-selective membrane between two planar microchips, each chip containing a microchannel, however this led to imperfect sealing of the device, resulting in gap formation around the membrane and thereby current leakage.

SUMMARY OF THE INVENTION

The invention provides, in one embodiment, a concentrating device comprising:
- a fluidic chip comprising a planar array of channels through which a liquid comprising a species of interest can be made to pass;
- at least one rigid substrate connected thereto such that at least a portion of a surface of the substrate bounds the channels;
- a high aspect ratio ion-selective membrane, embedded within the chip, attached to at least a portion of the channels;
- a unit to induce an electric field in the channel; and
- a unit to induce an electrokinetic or pressure driven flow in the channel.

In one embodiment, the means for inducing an electric field in the channel is a voltage supply, which in one embodiment is supplied at between 50 mV and 1500 V. In one embodiment, the voltage supply applies equal voltage to opposing sides of said microchannels, or in another embodiment, the voltage supply applies greater voltage to one channel, as compared to another channel, or in another embodiment, the voltage supply causes a potential difference between one area of said microchannel, as compared to another area within said microchannel. In another embodiment the voltage supply creates a potential difference between at least two said channels.

In one embodiment, the width of the channel is between about 0.1-500 μm, and in one embodiment, the width of the channel is between about 10 μm-200 μm. In some embodiments, the width of the channel is between about 100-1200 μm. In some embodiments the depth of the channel is between about 0.5-200 μm, and in some embodiments, the depth of the channel is between about 5-50 μm. In some embodiments the depth of the channel is between about 50-150 μm. In some embodiments, the ion-selective membrane has a width of between about 0.01-100 μm, and in some embodiments, the width of the ion-selective membrane is 1-10 μm. In some embodiments, the ion-selective membrane has a width of between about 100-500 nm. In some embodiments, the ion-selective membrane has a depth of between about 0.01-3000 μm, and in some embodiments, the depth of the ion-selective membrane is between about 10-500 μm and in some embodiments, the depth of the ion-selective membrane is between about 100-1000 μm. In some embodiments, the ion-selective membrane has a depth of between about 550-1050 μm.

In some embodiments, the rigid substrate comprises pyrex, silicon, silicon dioxide, silicon nitride, quartz, PMMA, PC or acryl.

In one embodiment, the fluidic chip comprises polydimethylsiloxane.

In one embodiment, the high aspect ratio ion-selective membrane comprises polytetrafluorethylenes (PTFEs), perfluorosulfonates, polyphosphazenes, polybenzimidazoles (PBIs), poly-zirconia, polyethyleneimine-poly(acrylic acid), poly(ethylene oxide)-poly(acrylic acid), or non-fluorinated hydrocarbon polymers or polymer-inorganic composites. In some embodiments the high aspect ratio ion selective membrane comprises sulfonated tetrafluorethylene copolymer. In some embodiments the sulfonated tetrafluoroethylene copolymer comprises Nafion or Nafion solution. In some embodiments the high aspect ratio ion selective membrane comprises microparticles or beads. In some embodiments the microparticles or beads comprises silica or polystyrene.

In some embodiments, the surface of the microchannel has been functionalized to reduce or enhance adsorption of said species of interest to said surface, or in some embodiments, the surface of the microchannel has been functionalized to enhance or reduce the operation efficiency of the device.

In some embodiments the high aspect ratio ion selective membrane is not in contact or is in minimal contact with the rigid substrate or the cover glass of the device.

In some embodiments, the unit to induce an electric field in the channel comprises at least a pair of electrodes and a power supply. In some embodiments, the substrate comprises electrodes, which are positioned proximally to the ion-selective membrane.

In some embodiments, the device is coupled to a separation system, detection system, analysis system or combination thereof. In some embodiments, the device is coupled to a mass spectrometer.

In one embodiment, the invention provides for a method of concentrating a species of interest in a liquid, the method comprising applying a liquid comprising the species of interest to the devices of this invention. In one embodiment the device comprising
  a fluidic chip comprising a planar array of channels through which a liquid comprising a species of interest can be made to pass;
  at least one rigid substrate connected thereto such that at least a portion of a surface of the substrate bounds the channels;
  a high aspect ratio ion-selective membrane, embedded within the chip, attached to at least a portion of the channels;
In one embodiment, the method further comprises the steps of:
  inducing an electric field in the channel whereby ion depletion occurs in a region in the channel proximal to the high aspect ratio ion-selective membrane embedded within the chip, and a space charge layer is formed within the channel, which provides an energy barrier to the species of interest; and
  inducing liquid flow in the channel.

In one embodiment, the flow is electroosmotic, or in another embodiment, the flow is pressure driven.

In one embodiment, the steps are carried out cyclically.

In one embodiment, inducing an electric field in said channel is by applying voltage to said device, which in one embodiment is between 50 mV and 1500 V. In one embodiment, equal voltage is applied to opposing sides of the channel, or in another embodiment, greater voltage is applied to the anodic side of the channel, as compared to the cathodic side.

In one embodiment, a space charge layer is generated in the channel prior to applying greater voltage to the anodic side of said channel.

In one embodiment, the liquid comprises an organ homogenate, cell extract or blood sample. In another embodiment, the species of interest comprises proteins, polypeptides, nucleic acids, viral particles, or combinations thereof.

According to this aspect of the invention and in another embodiment, the device is coupled to a separation system, detection system, analysis system or combination thereof. In some embodiments the detection system or analysis system comprises fluorescence. In one embodiment the high aspect ratio ion selective membrane is not in contact or is in minimal contact with the rigid substrate. In some embodiments such minimal or no contact eliminates or reduces contamination of the rigid substrate by fluorescent molecules. In some embodiments the concentration method results in large volumes of concentrated species in a liquid. In some embodiments the large concentrated volume containing the concentrated species is about 10 nL.

In some embodiments, this invention provides a method for the preparation of a concentrating device comprising:
  a fluidic chip comprising a planar array of channels through which a liquid comprising a species of interest can be made to pass;
  at least one rigid substrate connected thereto such that at least a portion of a surface of the substrate bounds the channels;
  a high aspect ratio ion-selective membrane, embedded within the chip, attached to at least a portion of the channels;
  the method comprising:
  forming a high aspect ratio trench in said fluidic chip, such that the trench is perpendicular to the long axis of the channels, and such that the trench depth equals or exceeds the depth of the channels in the fluidic chip;
  bending the fluidic chip parallel to the long axis of the trench, such that at least a portion of the trench becomes wider;
  applying a liquid polymer to an area proximal to one end of the trench such that the liquid polymer is allowed to flow along the trench and fill the trench.
  unbending the fluidic chip such that the liquid polymer is strongly adhered to the trench;
  providing conditions such that the liquid polymer forms a high aspect ratio ion selective membrane embedded in the trench; and
  optionally removing residues of the polymer from areas of the fluidic chip proximal to the trench;
  attaching the rigid substrate to the fluidic chip comprising channels such that the channels bound at least a portion of a surface of the substrate.

In some embodiments, the liquid polymer comprises polytetrafluorethylenes, polyphosphazenes, polybenzimidazoles (PBIs), poly-zirconia, polyethyleneimine-poly(acrylic acid), or poly(ethylene oxide)-poly(acrylic acid). In some embodiments the liquid polymer comprises sulfonated tetrafluorethylene copolymer. In some embodiments the sulfonated tetrafluorethylene copolymer comprises a Nafion solution or pure Nafion. In some embodiments the high aspect ratio ion selective membrane comprises microparticles or beads. In some embodiments the microparticles or beads comprises silica or polystyrene.

In some embodiments the liquid polymer at least partially fills the channels in an area proximal to the high aspect ratio ion selective membrane. In some embodiments the high aspect ratio ion selective membrane is not in contact or is in minimal contact with the rigid substrate. In some embodiments the invention provides for a concentrating device made by the process of preparing a concentrating device of the present invention.

In one embodiment, high aspect ratio means that the depth is much larger than the width. In one embodiment, high aspect ratio means that the depth is of the order of hundreds to thousands of microns, while the width is of the order of single microns. In some embodiments, the high aspect ratio ion selective membrane has a width of between 0.1-100 µm. In some embodiments, the high aspect ratio ion selective membrane has a width of between 1-6 µm. In some embodiments, the high aspect ratio ion selective membrane has a non uniform width. In some embodiments, the high aspect ratio ion selective membrane has a depth of between 10-1000 µm. In some embodiments, the high aspect ratio ion selective membrane has a depth of between 500-850 µm. In some embodiments, the high aspect ratio ion selective membrane has a depth of between 750-1250 µm. In one embodiment, providing conditions such that the liquid polymer forms a high aspect ratio ion selective membrane embedded in the trench is accomplished by heating the liquid polymer. In one embodiment heating is conducted at a temperature of about 95°c. In one embodiment heating is performed for about 10 minutes. In one embodiment, attaching the substrate to the fluidic chip is by plasma bonding. In one embodiment, the length of the high aspect ratio membrane is any length that is longer than the gap between microchannels or reservoirs and microchannels of this invention.

In some embodiments, the fluidic chip comprising channels having a width of between 10-200 µm. In some embodiments, the fluidic chip comprising channels having a depth of between 5-100 µm.

In some embodiments the rigid substrate comprises pyrex, silicon, silicon dioxide, silicon nitride, quartz, PMMA, PC or acryl. In some embodiments the fluidic chip comprises polydimethylsiloxane.

function of increasing trapping time. The data are shown for 10 mM phosphate buffer, pH=7 solution.

Figure 7:
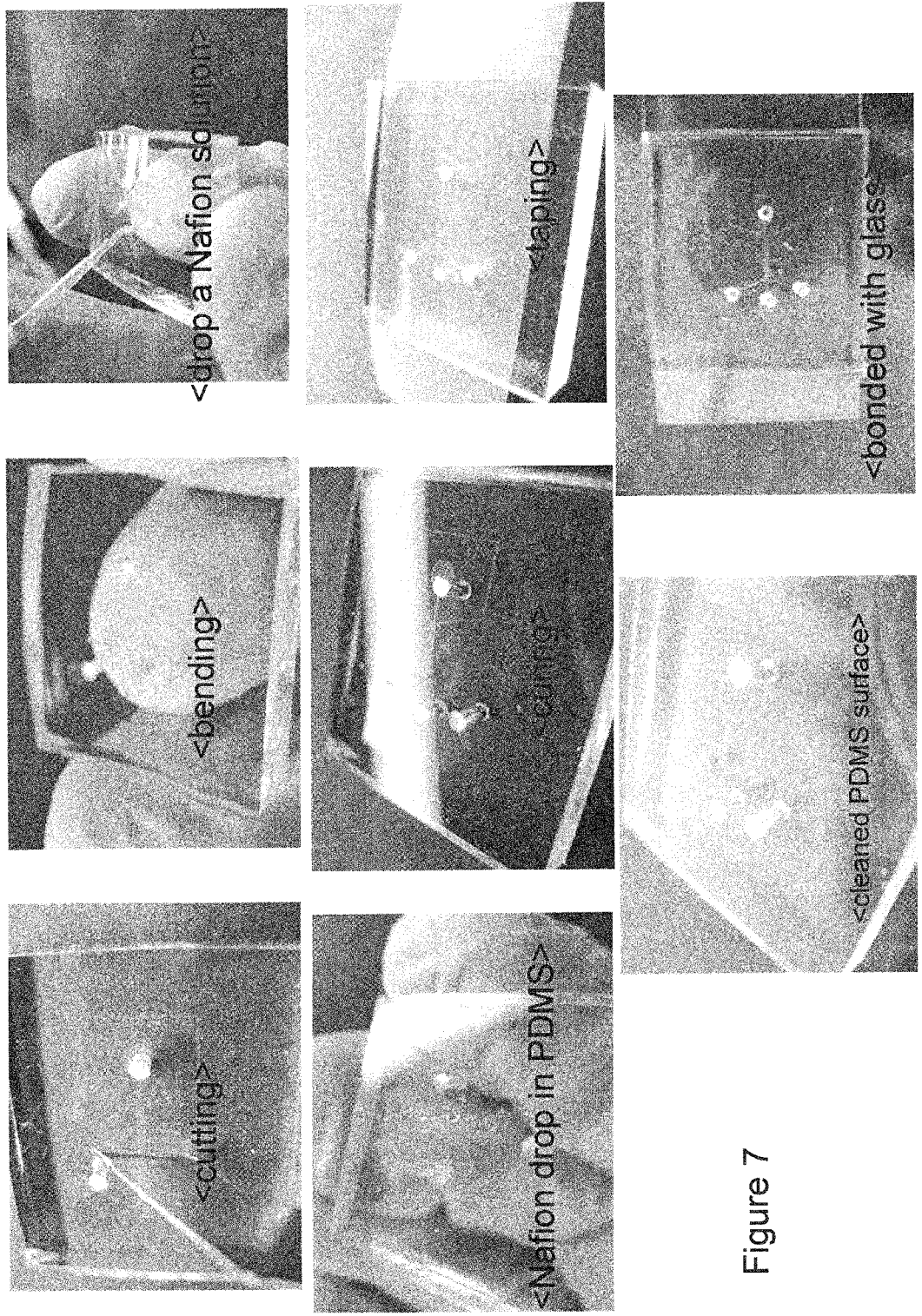

FIG. 7 depicts an embodiment of a device preparation procedure in which a trench is patterned in the PDMS chip and filled with Nafion. The Nafion is cured and sealed within the PDMS gap. A glass substrate is placed on top of the PDMS fluidic chip.

Figure 8:
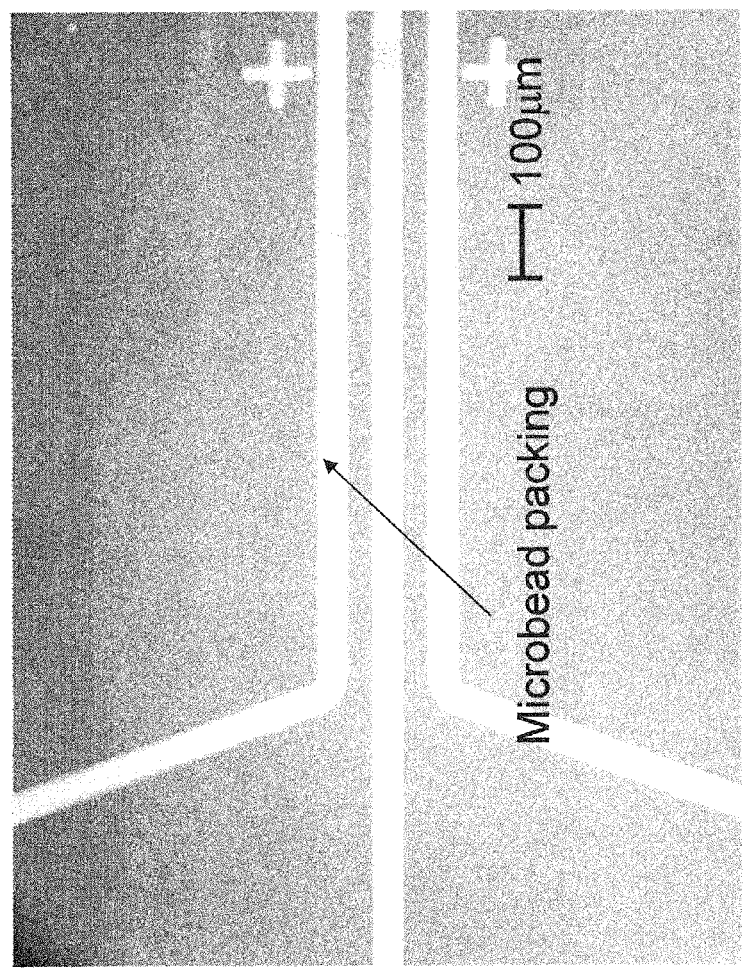

FIG. 8 is a device image of a microbead packed device fabricated using the self-sealed membrane method. The microbeads are polystyrene beads with 1 mm diameter. The gap between the beads is approximately 40 nm.

Figure 9:
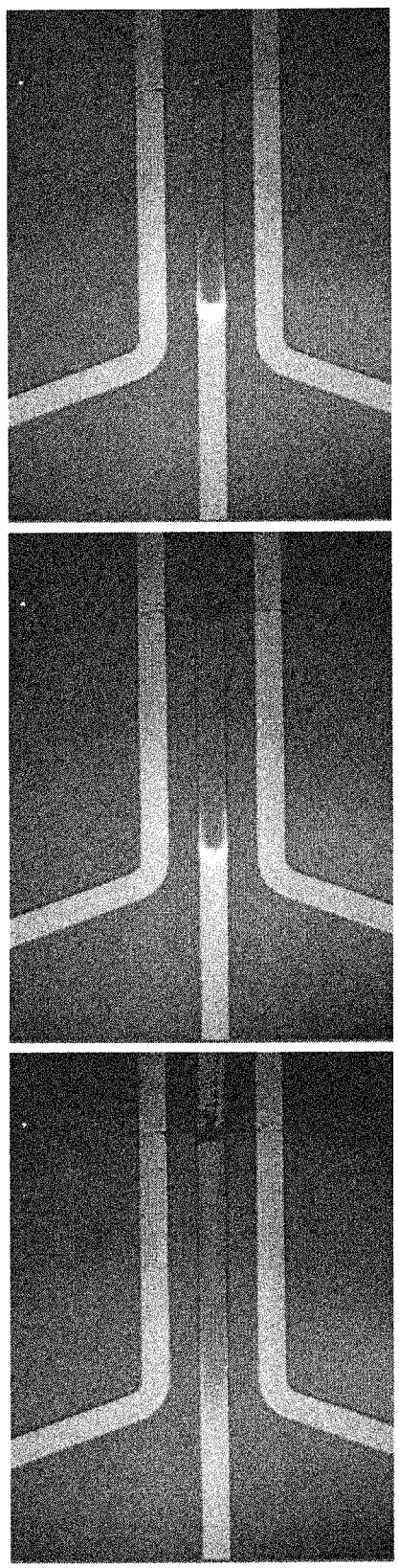

FIG. 9 depicts the preconcentration of a FITC dye in a device comprising a microbead packed high aspect ratio ion selective membrane.

DETAILED DESCRIPTION OF THE INVENTION

This invention provides, in one embodiment, a concentrating device and methods of use thereof, in concentrating a species of interest.

In some embodiments, this invention provides devices for concentration and/or pre-concentration of a substance on a micro- or nano-scale. The devices of this invention, in some embodiments, make use of high aspect ratio ion-selective membranes such as Nafion membranes, placed in microfluidic chips, through a unique fabrication process, which enables, in some embodiments, specific deposit of the ion-selective membrane in a device, in a manner, which is inexpensive and promotes ready deposition and high stability despite the known fragility of such membranes to physical manipulations, which in the past made their incorporation into such devices difficult.

In some embodiments, the devices and methods of this invention entail depositing, flowing or infiltrating resin solutions and curing such solutions to form the ion selective membranes, as herein described. In some embodiments, using the resin solution enables thin vertical membrane formation on a fluidic chip, and incorporation of the same adjacent to or in proximity to a microchannel of a device.

The invention provides, in one embodiment, a concentrating device comprising:
  a fluidic chip comprising a planar array of channels through which a liquid comprising a species of interest can be made to pass;
  at least one rigid substrate connected thereto such that at least a portion of a surface of the substrate bounds the channels;
  a high aspect ratio ion-selective membrane, embedded within the chip, attached to at least a portion of the channels;
  a unit to induce an electric field in the channel; and
  a unit to induce an electrokinetic or pressure driven flow in the channel.

In some embodiments, this invention provides a method for the preparation of a concentrating device comprising:
  a fluidic chip comprising a planar array of channels through which a liquid comprising a species of interest can be made to pass;
  at least one rigid substrate connected thereto such that at least a portion of a surface of the substrate bounds the channels;
  a high aspect ratio ion-selective membrane, embedded within the chip, attached to at least a portion of the channels;
  the method comprising
  forming a high aspect ratio trench in said fluidic chip, such that the trench is perpendicular to the long axis of the channels, and such that the trench depth equals or exceeds the depth of the channels in the fluidic chip;
  bending the fluidic chip parallel to the long axis of the trench, such that at least a portion of the trench becomes wider;
  applying a liquid polymer to an area proximal to one end of the trench such that the liquid polymer is allowed to flow along the trench and fill the trench.
  unbending the fluidic chip such that the liquid polymer is strongly adhered to the trench;
  providing conditions such that the liquid polymer forms a high aspect ratio ion selective membrane embedded in the trench; and
  optionally removing residues of the polymer from areas of the fluidic chip proximal to the trench;
  attaching the rigid substrate to the fluidic chip comprising channels such that the channels bound at least a portion of a surface of the substrate.

According to this aspect of the invention, and in one embodiment, this invention provides a device fabricated according to the preceding method.

In some embodiments, the liquid polymer comprises polytetrafluorethylenes, polyphosphazenes, polybenzimidazoles (PBIs), poly-zirconia, polyethyleneimine-poly(acrylic acid), or poly(ethylene oxide)-poly(acrylic acid).

In some embodiments, providing conditions such that the liquid polymer forms a membranous structure embedded within the chip is accomplished by heating the liquid polymer. In some embodiments the liquid polymer is heated to a temperature of about 95° c. In some embodiments the liquid polymer is heated for 10 minutes.

In one embodiment, attaching the substrate to the fluidic chip is by plasma bonding.

In one embodiment, the invention provides various methods for patterning an ion-selective membrane on a rigid substrate, to form the devices of this invention. Such methods are described herein, and exemplified in example 1 herein below.

In some embodiments, the patterning methods of this invention, and devices made thereby comprise, inter alia, flowing a resin through a micro- or nano-channel in a device under negative pressure, flushing the resin, and curing the adhered thin layer which in turn forms a membrane structure. In some embodiments, the viscosity of the resin is varied, or in some embodiments, the pressure applied is varied, which in turn will affect the thickness of the membrane formed thereby.

In some embodiments, the resin viscosity is varied, or in some embodiments, the hydrophobicity of the resin is varied, to affect the subsequent width of the ion-selective membrane formed thereby.

In some embodiments, curing the liquid polymer comprises, irradiation with UV light.

In some embodiments, the methods for producing micro- or nano-fluidic devices with high-aspect-ratio, ion-selective membranes of this invention, may comprise, inter alia, use of two oppositely charged polyelectrolytes such as PSS/PAA, which acts as s supporting solid matrix. Ion selectivity may then be imparted to the supporting matrix by infiltrating the membrane with a resin, which imparts such properties, for example, infiltrating the membrane with Nafion resin. According to this aspect of the invention and in one embodiment, due to the capillary force of the membrane, the pores of the polyelectrolyte membrane fill with the Nafion resin imparting to the membrane ion selectivity. In some embodiments, removing excess Nafion resin residue from the channel is accomplished by flushing the channel with deionized water.

It is to be understood that any liquid resin, or liquid polymer or a solution of monomers capable of polymerizing which when patterned and cured according to the methods as described herein, produces an ion-selective membrane is to be considered as part of this invention, and the invention is not to be limited to the examples of constituents of such resins as herein described.

In some embodiments, such membranes can be constructed so as to comprise a perfluorosulfonated membrane comprised of a polytetrafluoroethylene(PTFE)-crosslinked hydrophobic backbone impregnated with hydrophilic sulfonic acid sites. In some embodiments, hydrocarbon polymer non-fluorinated, and polymer-inorganic composite membranes can be similarly prepared, and used in the methods of this invention.

In some embodiments, the membranes/resins will comprise polymers such as polyphosphazenes, polybenzimidazoles (PBIs), and/or zirconia-polymer gels. In some embodiments the membrane comprises polyethyleneimine, polyacrylic acid, perfluorosulfonates, non-fluorinated hydrocarbon polymers, polymer-inorganic composites, polyethylene oxide or porous silica or alumina polymers.

In some embodiments, polyelectrolyte multilayer systems such as LPEI/PAA or PEO/PAA (LPEI: linear polyethyleneimine, PAA:poly(acrylic acid); PEO: poly(ethylene oxide)) may be used to form the membrane. In some embodiments, films constructed from LPEI and PAA exhibit an ionic conductivity as high as $10^{-5}$ S/cm$^{-1}$ at 100% relative humidity and room temperature, and thus are useful in the devices of this invention.

In some embodiments, a membrane of PEO and PAA can be constructed via hydrogen-bonding interactions, films with conductivities from $10^{-5}$ to as high as $10^{-4}$ S/cm$^{-1}$ at ambient conditions may be obtained. In some embodiments, the method comprising flowing a resin through a micro- or nano-channel in a device under negative pressure, flushing the resin, and curing the adhered thin layer is useful for producing the desired ion-selective membrane in the devices of this invention, using polyelectrolyte multilayers as described hereinabove.

In some embodiments, unique to the methods and devices of this invention is the absence of a requirement for the physical manipulation of fragile membranes in order to integrate such membranes into the devices of this invention. In some embodiments, the invention comprises processes for patterning/depositing a resin into a trench in the fluidic chip followed by curing of the resin to form a membrane, which in turn is readily integrated in the device without further physical manipulation of the formed membrane. In some embodiments, the devices of this invention and processes for preparing the same comprise curing a resin to form the membrane, as part of the construction of the device, and makes use of materials which are disposable, thus providing a simply manufactured device, which can readily be mass produced, to form arrays of parallel concentrators on a medium that can be disposable.

In some embodiments, the methods for producing micro- or nano-fluidic devices with ion-selective membranes of this invention, may comprise, the preparation of a high-aspect-ratio ion selective membrane, as exemplified in some embodiments herein. In some embodiments, such method may comprise building a high-aspect ratio membrane with a microbead-based approach, as will be appreciated by one skilled in the art. Self-assembled colloidal particles may be infiltrated with a resin, for example, Nafion, as described herein. In some embodiments the microparticles may be filtrated without a resin to form the membrane. In some embodiments the microparticles are referred to as beads. In some embodiments the beads or microparticles comprises silica or polystyrene. In some embodiments the spaces between the packed beads form the pores needed for fluid flow or for ion-passage. In some embodiments microparticles or bead size is 1 micron. In some embodiments the microparticle size is between 250 nm and 2 microns. In another embodiment, a trench, which is filled with the resin may be used to build the high-aspect ratio membrane. In one embodiment the trench is formed by cutting through the chip. In one embodiment the cut is done using a razor blade. In one embodiment the cut is done using a sharp object. In one embodiment the cut is done using a needle. In one embodiment the trench is made by lithography. In one embodiment the trench is made by UV lithography and in another embodiment by e-beam lithography. In one embodiment the trench is done using etching techniques. In one embodiment etching is dry and in another embodiment etching is wet.

The invention provides concentrating or pre-concentrating devices. In some embodiments, the concentrating device, which is referred to as a "concentrator", in another embodiment, comprises at least one microchannel and/or at least one nanochannel, placed on a PDMS substrate in a roughly planar format, wherein the channel is proximal to an ion-selective membrane, and the channel is bounded by a rigid substrate.

In one embodiment, the fluidic chip comprising a planar array of channels through which a liquid comprising a species of interest can be made to pass is formed using the technology of microfabrication and nanofabrication, for formation of the respective channels.

Microfabrication technology, or microtechnology or MEMS, in one embodiment, applies the tools and processes of semiconductor fabrication to the formation of, for example, physical structures. Microfabrication technology allows one, in one embodiment, to precisely design features (e.g., wells, channels) with dimensions in the range of <1 mm to several centimeters on chips made, in other embodiments, of silicon, glass, or plastics. Such technology may be used to construct the microchannels of the concentrator, in one embodiment.

In another embodiment, construction of the microchannels of the concentrator may be accomplished according to, or based upon any method known in the art, for example, as described in Z. N. Yu, P. Deshpande, W. Wu, J. Wang and S. Y. Chou, Appl. Phys. Lett. 77 (7), 927 (2000); S. Y. Chou, P. R. Krauss, and P. J. Renstrom, Appl. Phys. Lett. 67 (21), 3114 (1995); Stephen Y. Chou, Peter R. Krauss and Preston J. Renstrom, Science 272, 85 (1996) and U.S. Pat. No. 5,772,905 hereby incorporated herein, in their entirety, by reference. In one embodiment, the microchannels can be formed by imprint lithography, interference lithography, self-assembled copolymer pattern transfer, spin coating, electron beam lithography, focused ion beam milling, photolithography, reactive ion-etching, wet-etching, plasma-enhanced chemical vapor deposition, electron beam evaporation, sputter deposition, stamping, molding scanning probe techniques and combinations thereof. In some embodiments, the methods for preparation of the devices of this invention may comprise or be modifications of Astorga-Wells J. et al, Analytical Chemistry 75: 5207-5212 (2003); or Joensson, M. et al, Proceedings of the MicroTAS 2006 Symposium, Tokyo Japan, Vol. 1, pp. 606-608. Alternatively, other conventional methods can be used to form the microchannels.

In one embodiment, the microchannels are formed as described in J. Han, H. G. Craighead, J. Vac. Sci. Technol., A 17, 2142-2147 (1999) and J. Han, H. G. Craighead, Science 288, 1026-1029 (2000), hereby incorporated fully herein by reference.

In one embodiment, a series of reactive ion etchings are conducted, after which nano- or micro-channels are patterned with standard lithography tools. In one embodiment, the etchings are conducted with a particular geometry, which, in another embodiment, determines the interface between the microchannels, and/or nanochannels. In one embodiment, etchings, which create the microchannels, are performed parallel to the plane in which etchings for the nanochannels are created. In another embodiment, additional etching, such as, for example, and in one embodiment, KOH etching is used, to produce additional structures in the concentrator, such as, for example, for creating loading holes.

In another embodiment, electrical insulation of the concentrator is accomplished. In one embodiment, such insulation is accomplished via nitride stripping and thermal oxidation of the concentrator. In another embodiment, a surface of the concentrator, which in another embodiment is the bottom surface, may be affixed to a substrate, such as, for example, and in one embodiment, a Pyrex wafer. In one embodiment, the wafer may be affixed using anodic bonding techniques.

In one embodiment, construction of the fluidic chip comprising a planar array of channels may be accomplished by methods known to one skilled in the art, or adaptation of such methods, such as, for example those described in U.S. Pat. No. 6,753,200, fully incorporated herein by reference.

In one embodiment, the fabrication may use a shaped sacrificial layer, which is sandwiched between permanent floor and ceiling layers, with the shape of the sacrificial layer defining a working gap. When the sacrificial layer is removed, the working gap becomes a fluid channel having the desired configuration. This approach, in one embodiment, allows a precise definition of the height, width and shape of interior working spaces, or fluid channels, in the structure of a fluidic device.

The sacrificial layer is formed on a substrate, is shaped by a suitable lithographic process, for example, and is covered by a ceiling layer. Thereafter, the sacrificial layer may be removed with a wet chemical etch, leaving behind empty spaces between the floor and ceiling layers which form working gaps which may be used as flow channels and chambers for the concentrator. In such a device, the vertical dimension, or height, of a working gap is determined by the thickness of the sacrificial layer film, which is made with precise chemical vapor deposition (CVD) techniques, and accordingly, this dimension can be very small.

In order to provide access to the sacrificial layer contained in the structure for the etching solution, which is used to remove the sacrificial layer, one or more access holes may be cut through the ceiling layer, with the wet etch removing the sacrificial layer through these holes. An extremely high etch selectivity may be required between the sacrificial layer and the dielectric layers in order to allow the etch to proceed in the sacrificial layer a significant distance laterally from the access holes without consuming the floor and ceiling layers which compose the finished device. One combination of materials, which may be used for such a process is polysilicon and silicon nitride, for the sacrificial layer and for the floor and ceiling layers, respectively. Extremely high etch selectivities can be obtained with basic solutions such as, in some embodiments, potassium hydroxide (KOH), sodium hydroxide (NaOH), or in another embodiment, tetramethyl ammonium hydroxide (TMAH).

In some embodiments, the ceiling layer is the rigid substrate with which the ion-selective membrane is associated.

The access holes cut in the top layer may be covered, in another embodiment. For this purpose, a sealing layer of silicon dioxide may be deposited on top of the ceiling lay to fill in the access holes, and this additional thin film layer provides a good seal against leakage or evaporation of fluids in the working gap. $SiO_2$ CVD techniques, represent other embodiments, which yield a low degree of film conformality, such as very low temperature oxide (VLTO) deposition, form a reliable seal without excessive loss of device area due to clogging near the access holes. If desired, the access holes may be drilled through the bottom layer, instead of or in addition to the holes in the ceiling layer, and later resealed by depositing a layer of silicon dioxide.

For example, in some embodiments, chemical vapor deposition (CVD) may be used to deposit the device materials, including permanent wall materials, which are usually a dielectric material such as silicon nitride or silicon dioxide, and nonpermanent sacrificial layer materials, such as amorphous silicon or polysilicon.

In some embodiments, micro-channels and/or nano-channels are oriented in parallel on the chip, forming an array of channels, wherein each channel may represent a concentrator, such that multiple parallel concentrations may be accomplished on a single chip. In some embodiments, the channels intersect, such that material concentrated in a channel can, under appropriate conditions be conveyed to another concentrator on the chip, for example, post assay or exposure to a particular reagent. According to this aspect, and in some embodiments, the array or channels, which intersect, allow for multi-step concentration, for example following manipulation or exposure to a dilute environment, and repeat concentration is desirable.

In some embodiments, the microchannels are positioned in any desired orientation, for example as befitting to suit a particular purpose or collection scheme, etc. axis of another.

In one embodiment, an interface region is constructed which connects the channels on the chip, for example two microchannels of the concentrator of this invention. In one embodiment, diffraction gradient lithography (DGL) is used to form a gradient interface between the channels of this invention, where desired. In one embodiment, the gradient interface region may regulate flow through the concentrator, or in another embodiment, regulate the space charge layer formed in the microchannel, which, in another embodiment, may be reflected in the strength of electric field, or in another embodiment, the voltage needed to generate the space charge layer in the microchannel. In some embodiments, the ion-selective membrane is positioned at such an interface.

In one embodiment, the gradient interface area is formed of lateral spatial gradient structures for narrowing the cross section of a value on a desired scale, for example, from the micron to the nanometer length scale. In another embodiment, the gradient interface area is formed of a vertical sloped gradient structure. In another embodiment, the gradient structure can provide both a lateral and vertical gradient.

In one embodiment, the concentrating device may be fabricated by diffraction gradient lithography, by forming a microchannel or microchannels on a substrate and forming a gradient interface area between the desired channels. The gradient interface area can be formed, in one embodiment, by using a blocking mask positioned above a photo mask and/or photoresist during photolithography. The edge of the blocking mask provides diffraction to cast a gradient light intensity on the photoresist.

In one embodiment, a concentrator may comprise a plurality of channels, including a plurality of microchannels, and/or a plurality of nanochannels, or a combination thereof. In one embodiment, the phrase "a plurality of channels refers to more than two channels, or, in another embodiment, more than 5, or, in other embodiments, more than 10, 96, 100, 384, 1,000, 1,536, 10,000, 100,000 or 1,000,000 channels, or in any number desired to suit a particular purpose. Similarly, arrangement of the channels on the chip may be so designed as to suit a particular application.

In one embodiment, a device may contain a plurality of high aspect ratio, ion selective membranes. In one embodiment a plurality of high-aspect ratio ion selective membranes can be fabricated on a chip. In one embodiment fabrication of a plurality of high-aspect ratio ion selective membranes may be done using multi-blade fabrication. In one embodiment multi-blade fabrication can be used for commercialization of a device containing a self-sealed membrane. In one embodiment a self-sealed membrane refers to the high aspect ratio ion selective membrane. In one embodiment "self-sealed" means that after infiltration, or passage or filling of the trench or the gap, or the scratch made by the blade with a liquid polymer solution, unbending the chip and solidifying the polymer causes a self-sealing process of the scratch or the gap or the trench by the polymer.

In one embodiment, multi-blade fabrication can be used for massive parallelization of the membrane or the device fabrication process. In one embodiment, multi-blade fabrication can be used to make a plurality of membranes in parallel. In one embodiment, multi-blade fabrication renders the fabrication process fast. In one embodiment, multi-blade fabrication renders the device a low-cost device. In one embodiment multi-blade fabrication is combined with multi-syringe or multi dispenser system that enables parallel injection of liquid polymer to all trenches or cuts made by the multiple blades. In one embodiment the multi-blade fabrication technique is part of an automated fabrication technique, in which all steps of forming the high aspect ratio ion selective membranes are automated, and all steps are performed in parallel on many channels or on many device parts or on many devices. In one embodiment such automation enables mass production of devices, low cost, high yield and reproducibility of device properties. In one embodiment parallel multi-blade fabrication facilitates quality control and reliability measurements to be done on selected devices. In one embodiment multi-blade fabrication and/or automation of the process are achieved using computers, computer programs, robotics or a combination thereof. In one embodiment the number of high aspect ratio ion selective membranes produced is equal to the number of channels described herein above. In one embodiment the number of high aspect ratio ion selective membranes produced is greater than the number of channels described herein above. In one embodiment the number of high aspect ratio ion selective membranes produced is smaller than the number of channels described herein above. In one embodiment the number of high aspect ratio ion selective membranes produced is more than 5, or, in other embodiments, more than 10, 96, 100, 384, 1,000, 1,536, 10,000, 100,000 or 1,000,000 channels, or in any number desired to suit a particular purpose.

In one embodiment, the width of the microchannel is between 1-100 µm, or in another embodiment, between 1 and 15 µm, or in another embodiment, between 20 and 50 µm, or in another embodiment, between 25 and 75 µm, or in another embodiment, between 50 and 100 µm or in another embodiment, between 0.1 and 500 µm, or in another embodiment, between 10 and 25 µm, or in another embodiment, between 100 and 1200 µm. In one embodiment, the depth of the microchannel is between 0.5-50 µm, or in another embodiment, between 0.5 and 5 µm, or in another embodiment, between 5 and 15 µm, or in another embodiment, between 10 and 25 µm, or in another embodiment, between 15 and 50 µm, or in another embodiment, between 1 µm-50 µm, or in another embodiment, between 10 and 25 µm, or in another embodiment, between 15 and 40 µm, or in another embodiment, between 0.5 and 200 µm. In another embodiment, the depth of the channel is between 1 µm-50 µm, or in another embodiment, between 5 and 25 µm, or in another embodiment, between 5 and 50 µm, or in another embodiment, between 25 and 50 µm, or in another embodiment between 50 and 150 µm.

In one embodiment, the concentrator is constructed as shown in FIG. 7 or according to the schematic provided in FIG. 1. The microchannels, are oriented in parallel on a PDMS chip (FIG. 1a), and a cut is made perpendicular to the long axis of the channels (FIG. 1b). The PDMS chip is bent such that the gap formed by the cut is opened and become wider (FIG. 1c). A drop of liquid polymer, microparticles, a solution thereof or a combination thereof is introduced proximal to one end of the gap (FIG. 1d). A cover glass or another rigid substrate is plasma bonded to the chip (FIG. 1e). Photographs corresponding to the various process steps are shown in FIG. 7.

In one embodiment the high aspect ratio ion selective membrane has a width of between 0.01-100 µm. In one embodiment the high aspect ratio ion selective membrane has a width of between 1-10 µm. In one embodiment the high aspect ratio ion selective membrane has a width of between 0.1-0.5 µm. In one embodiment the high aspect ratio ion selective membrane has a width of between 2-4 µm. In one embodiment the high aspect ratio ion selective membrane has a width of between 2-8 µm. In one embodiment the high aspect ratio ion selective membrane has a width of between 1-20 µm. In one embodiment the high aspect ratio ion selective membrane has a width of between 10-20 µm. In one embodiment the high aspect ratio ion selective membrane has a width of between 0.01-0.1 µm.

In one embodiment the high aspect ratio ion selective membrane has a depth of between 0.01-3000 µm. In one embodiment the high aspect ratio ion selective membrane has a depth of between 10-500 µm. In one embodiment the high aspect ratio ion selective membrane has a depth of between 100-1000 µm. In one embodiment the high aspect ratio ion selective membrane has a depth of between 550-1050 µm. In one embodiment the high aspect ratio ion selective membrane has a depth of between 75-125 µm. In one embodiment the high aspect ratio ion selective membrane has a depth of between 1000-2000 µm. In one embodiment the high aspect ratio ion selective membrane has a depth of between 100-550 µm. In one embodiment the high aspect ratio ion selective membrane has a depth of between 200-800 µm or in another embodiment the ion selective membrane has a depth of 1-100 µm. In one embodiment the depth or width or a combination thereof of the high aspect ratio ion selective membrane are non uniform. In one embodiment the depth of the membrane is measured from the top of the PDMS chip and in one embodiment the depth of the membrane is measured from the bottom of the channels.

In some embodiments the chip comprises polydimethylsiloxane (PDMS).

In one embodiment the high aspect ratio ion selective membrane is embedded within the chip. In one embodiment "embedded" means confined, adhered to, placed between, shielded by, is part of, protected by, covered by or pressed between at least a portion of the chip. In some embodiments the membrane is formed by introducing a liquid polymer or a solution containing microparticles or nanoparticles to a trench in the chip. In some embodiments the polymer solution or polymer or a solution or mixture of monomers or beads is cured within the trench. In some embodiments while curing the polymer or the membrane material, the two walls of the trench are pressed together or are held tightly by releasing from a bended orientation. In some embodiments curing the membrane material involves bond formation between the trench walls and the membrane material. In some embodiments the bonds are covalent. In some embodiments the bonds are polar or van der Waals bonds. In some embodiments the membrane material and the walls of the trench are held together mechanically. In some embodiments the trench in the chip can be bent to open. In some embodiments bending widens the trench. In some embodiments bending results in a non-uniform width of the trench. In some embodiments bending allows the easy passage of liquid membrane material through the trench. In one embodiment the term "trench" refers to a slit, a gap, a space, a channel, or a hole, in the chip of this invention.

In one embodiment the high aspect ratio ion selective membrane is attached to at least a portion of the channels. In one embodiment the membrane is attached to the bottom and to the walls of the channels in the area in which the cut or trench was made. In some embodiments when the membrane liquid material is infiltrated through the trench, a portion of it fills the channels in the area proximal to the trench. In some embodiments residues of membrane material within the channels are removed. In some embodiments the residues are removed by taping the surface of the chip and peeling the tape. In some embodiments membrane material on the surface of the chip and in the channels, adheres to the tape and is peeled off the chip when peeling the tape. In some embodiments the tape is a simple adhesive tape.

In one embodiment "high aspect ratio membrane" means a vertical membrane. In one embodiment "high aspect ratio membrane" means a membrane in which the depth exceeds the width. In some embodiments the depth is 25 folds larger than the width. In some embodiments the depth is 100 folds larger than the width. In some embodiments the depth is 250 folds larger than the width. In some embodiments the depth exceeds the width by any amount that fits a certain application of the present invention. In some embodiments "ion selective" means that only a certain type of ions can enter the membrane. In some embodiment ion selective refers to the size of the ions, the charge of the ions, shape or a combination thereof. In some embodiments ions can be organic or inorganic. In some embodiments the membrane is permeable to protons (positive hydrogen ions) only. In some embodiments ion-selective means that a membrane can pass ions and can prevent the passage or transfer of uncharged species. In one embodiment the membrane is permeable to positive ions only, and is not permeable toward anions and electrons.

In one embodiment a method for the preparation of a device of this invention minimizes contact between the membrane material and the glass or cover substrate of the chip. In one embodiment only a thin portion of the membrane material touches the cover glass. In one embodiment such configuration reduces the contact between contaminating molecules in the sample that are trapped in the membrane and the cover glass. In some embodiments, fluorescent molecules that are trapped or are passing through the membrane can interfere with a sample fluorescent signal, if the membrane area proximal to the cover glass is extensively large. In one embodiment of the present invention, having the membrane embedded in the chip as opposed to covering the glass, results in enhanced fluorescence signal resolution and clarity.

In another aspect of the invention, the concentrator further comprises at least one sample reservoir in fluid communication with the microchannel or microchannels. In another embodiment, the sample reservoir is capable of releasing a fluid or liquid comprising a species of interest. In one embodiment, the sample reservoir is connected to the microchannel by means of a conduit, which may have the dimensions of the microchannel, or may comprise a gradient interface area, as described.

In one embodiment, the introduction of a liquid comprising a species of interest in the device and independent induction of an electric field in the nanochannel and/or in the microchannel, concentrates the species of interest within the channel.

In one embodiment, the concentrator makes use of an ion-selective membrane to generate ion-depletion regions for electrokinetic trapping, as exemplified and described herein.

In one embodiment, an electric field is applied to the concentrator and generates an ion-depletion region and extended space charge layer that traps anionic molecules. A tangential field in the anodic side may generate electroosmotic flow, which draws molecules into a trapped region.

In one embodiment, flow in the device may be pressure-driven, and may be accomplished by any means well known to one skilled in the art. In another embodiment, the flow may be a hybrid of pressure-driven and electrokinetic flow.

In one embodiment, the phrases "pressure-driven flow" refers to flow that is driven by a pressure source external to the channel segment through which such flow is driven, as contrasted to flow that is generated through the channel segment in question by the application of an electric field through that channel segment, which is referred to herein, in one embodiment, as "electrokinetically driven flow."

Examples of pressure sources include negative and positive pressure sources or pumps external to the channel segment in question, including electrokinetic pressure pumps, e.g., pumps that generate pressure by electrokinetically driven flow in a pumping channel that is separate from the channel segment in question, provided such pumps are external to the channel segment in question (see, U.S. Pat. Nos. 6,012,902 and 6,171,067, each of which is incorporated herein by reference in its entirety for all purposes).

In one embodiment, the term "electrokinetic flow" refers to the movement of fluid or fluid borne material under an applied electric field. Electrokinetic flow generally encompasses one or both of electrophoresis, e.g., the movement of charged species through the medium or fluid in which it is disposed, as well as electroosmosis, e.g., the electrically driven movement of the bulk fluid, including all of its components. Accordingly, when referred to in terms of electrokinetic flow, it will be appreciated that what is envisioned is the full spectrum of electrokinetic flow from predominantly or substantially completely electrophoretic movement of species, to predominantly electroosmotically driven movement of material, e.g., in the case of uncharged material, and all of the ranges and ratios of the two types of electrokinetic movement that fall between these extremes.

In one embodiment, reference to the term "liquid flow" may encompass any or all of the characteristics of flow of fluid or other material through a passage, conduit, channel or across a surface. Such characteristics include without limitation the flow rate, flow volume, the conformation and accompanying dispersion profile of the flowing fluid or other material, as well as other more generalized characteristics of flow, e.g., laminar flow, creeping flow, turbulent flow, etc.

In one embodiment, hybrid flow may comprise pressure-based relay of the liquid sample into the channel network, followed by electrokinetic movement of materials, or in another embodiment, electrokinetic movement of the liquid followed by pressure-driven flow.

In one embodiment, the electric field may be induced in the respective channels by applying voltage from a voltage supply to the device. In one embodiment voltage is applied by way of the placement of at least one pair of electrodes capable of applying an electric field across at least some of the channels in at least one direction. Electrode metal contacts can be integrated using standard integrated circuit fabrication technology to be in contact with at least one microchannel, or in another embodiment, at least one nanochannel, or in another embodiment, a combination thereof, and oriented as such, to establish a directional electric field. Alternating current (AC), direct current (DC), or both types of fields can be applied. The electrodes can be made of almost any metal, and in one embodiment, comprise thin Al/Au metal layers deposited on defined line paths. In one embodiment, at least one end of one electrode is in contact with buffer solution in the reservoir.

In another embodiment, the concentrator may contain at least two pairs of electrodes, each providing an electric field in different directions. In one embodinet, field contacts can be used to independently modulate the direction and amplitudes of the electric fields to, in one embodiment, orient the space charge layer, or in another embodiment, move macromolecules at desired speed or direction, or in another embodiment, a combination thereof.

In one embodiment, the voltage applied is between 50 mV and 1500 V. In one embodiment, the voltage supply applies equal voltage to opposing sides of the microchannel, or in another embodiment, the voltage supply applies greater voltage to the anodic side of said microchannel, as compared to the cathodic side. In one embodiment, the voltage supply applies voltage across a microchannel. In one embodiment, the voltage across the microchannel is applied such that the connection between the microchannel and a nanochannel is in between the two points to which voltage is applied. In one embodiment, a higher positive voltage is applied to one end of a microchannel and a lower positive voltage is applied to the other end of the microchannel such that the connection between the microchannel and a nanochannel is between these two ends. In one embodiment, the end of the nanochannel that is farther away from the microchannel is grounded. In one embodiment, 10 V are applied to one end of the microchannel, 5 V are applied to the other end of the microchannel and the microchannel is connected to a nanochannel such that the end of the nanochannel that is far from the microchannel is electrically grounded. In one embodiment, equal voltage is applied to the two ends of the microchannel on two sides of the connection area between the nanochannel and the microchannel.

In one embodiment, instead of an array of microchannels, devices and methods of this invention comprise only one microchannel and one nanochannel or only two microchannels and one nanochannel, or only two nanochannels and one microchannel, or any number of microchannels and nanochannels between one (1) and ten (10).

In one embodiment, the voltage supply may be any electrical source, which may be used to provide the desired voltage. The electrical source may be any source of electricity capable of generating the desired voltage. For example, the electrical source may be a piezoelectrical source, a battery, or a device powered by household current. In one embodiment, a piezoelectrical discharge from a gas igniter may be used.

In one embodiment, the electrokinetic trapping in the device and sample collection can occur over a course of minutes, or in another embodiment, can be maintained for several hours. In one embodiment, concentration over a course of time results in concentration factors as high as $10^6$-$10^8$, and in another embodiment, may be even higher, upon optimization of the conditions employed during the concentration, such as by modifying the voltage applied, salt concentration of the liquid, pH of the liquid, ion-selective membrane choice of materials or thickness or combination thereof.

In another embodiment, the concentrator further comprises at least one waste reservoir in fluid communication with the microchannel, microchannels, nanochannel and/or nanochannels of the concentrator. In one embodiment, the waste reservoir is capable of receiving a fluid.

In one embodiment, the surface of the microchannel may be functionalized to reduce or enhance adsorption of the species of interest to the surface of the concentrator. In another embodiment, the surface of the nanochannel and/or microchannel has been functionalized to enhance or reduce the operation efficiency of the device. In another embodiment, external gate potential is applied to the substrate of the device, to enhance or reduce the operation efficiency of the device. In another embodiment, at least part of the device is comprised of a transparent material. In another embodiment, the transparent material is pyrex, silicon dioxide, silicon nitride, quartz, PMMA, PC or acryl.

In another embodiment, the concentrator is adapted such that analysis of a species of interest may be conducted, in one embodiment, in the concentrator, or in another embodiment, downstream of the concentrator. In one embodiment, analysis downstream of the concentrator refers to removal of the concentrated species from the device, and placement in an appropriate setting for analysis, or in another embodiment, construction of a conduit from the concentrator which relays the concentrated material to an appropriate setting for analysis. In one embodiment, such analysis may comprise signal acquisition, and in another embodiment, a data processor. In one embodiment, the signal can be a photon, electrical current/impedance measurement or change in measurements. It is to be understood that the concentrating device of this invention may be useful in various analytical systems, including bioanalysis Microsystems, due to its simplicity, performance, robustness, and integrability to other separation and detection systems, for example as described herein below and depicted in FIG. 5. It is to be understood that any integration of the device into such a system is to be considered as part of this invention.

In another embodiment, the concentrator, or in another embodiment, the microchannel or microchannels are capable of being imaged with a two-dimensional detector. Imaging of the concentrator, or parts thereof, may be accomplished by presenting it to a suitable apparatus for the collection of emitted signals, such as, in some embodiments, optical elements for the collection of light from the microchannels.

In another embodiment, the device is coupled to a separation system, or in another embodiment, a detection system, or in another embodiment, an analysis system or in another embodiment, a combination thereof. In one embodiment the device is coupled to a mass spectrometer. In another embodiment, the device is coupled to an illumination source. According to this aspect, and in some embodiments, assay of concentrated materials may be accomplished within devices as herein described, and their analysis may be affected by coupling appropriate detection apparatus and systems to the device to conduct such analysis. In some embodiments, such assay may be enzymatic assay, probe detection of a desired product, synthetic procedures, digestion of materials, or others as will be appreciated by one skilled in the art. In some embodiment detection or analysis is done using fluorescence techniques. In one embodiment a fluorescent marker is bound to the species of interest. In one embodiment an illumination source illuminates the channels containing the species. In one embodiment fluorescence caused by illumination of the fluorescent marker is detected by a light detector. In some embodiments the concentration of the marker and of the species of interest can be measured quantitatively. In one embodiment such measurement can detect the location and concentration of the species of interest. In some embodiments location and concentration of species of interest can be detected as a function of time.

In one embodiment, the concentrator may be disposable, and in another embodiment, may be individually packaged, and in another embodiment, have a sample loading capacity of 1-50,000 individual fluid samples. In one embodiment, the concentrator can be encased in a suitable housing, such as plastic, to provide a convenient and commercially-ready cartridge or cassette. In one embodiment, the concentrator will have suitable features on or in the housing for inserting, guiding, and aligning the device, such that, for example, a sample loading compartment is aligned with a reservoir in another device, which is to be coupled to the concentrator. For example, the concentrator may be equipped with insertion slots, tracks, or a combination thereof, or other adaptations for automation of the concentration process via a device of this invention.

The concentrator may be so adapted, in one embodiment, for high throughput screening of multiple samples, such as will be useful in proteomics applications, as will be appreciated by one skilled in the art.

In one embodiment, the concentrator is connected to electrodes, which are connected to an electric potential generator, which may, in another embodiment be connected with metal contacts. Suitable metal contacts can be external contact patches that can be connected to an external scanning/imaging/electric-field tuner, in another embodiment.

In one embodiment of the present invention, the concentrator is a part of a larger system, which includes an apparatus to excite molecules inside the channels and detect and collect the resulting signals. In one embodiment, a laser beam may be focused upon the sample plug, using a focusing lens, in another embodiment. The generated light signal from the molecules inside the microchannels may be collected by focusing/collection lens, and, in another embodiment, reflected off a dichroic mirror/band pass filter into optical path, which may, in another embodiment, be fed into a CCD (charge coupled device) camera.

In another embodiment, an exciting light source could be passed through a dichroic mirror/band pass filter box and focusing/collecting scheme from the top of the concentrator. Various optical components and devices can also be used in the system to detect optical signals, such as digital cameras, PMTs (photomultiplier tubes), and APDs (Avalanche photodiodes).

In another embodiment, the system may further include a data processor. In one embodiment, the data processor can be used to process the signals from a CCD, to a digital image of the concentrated species onto a display. In one embodiment, the data processor can also analyze the digital image to provide characterization information, such as size statistics, histograms, karyotypes, mapping, diagnostics information and display the information in suitable form for data readout.

In one embodiment, the device is further modified to contain an active agent in the microchannel. For example, and in one embodiment, the microchannel is coated with an enzyme at a region wherein the concentrated molecules will be trapped, according to the methods of this invention. According to this aspect, the enzyme, such as, a protease, may come into contact with concentrated proteins, and digest them. According to this aspect, the invention provides a method for proteome analysis, wherein, for example, a sample comprising a plurality of cellular polypeptides is concentrated in the microchannel, to obtain a plurality of substantially purified polypeptides. The polypeptide is exposed to a protease immobilized within the microchannel, under conditions sufficient to substantially digest the polypeptide, thereby producing digestion products or peptides. The digestion products may, in another embodiment, then be transported to a downstream separation module where they are separated, and in another embodiment, from there, the separated digestion products may be conveyed to a peptide analysis module. The amino acid sequences of the digestion products may be determined and assembled to generate a sequence of the polypeptide. Prior to delivery to a peptide analysis module, the peptide may be conveyed to an interfacing module, which in turn, may perform one or more additional steps of separating, concentrating, and or focusing.

In other embodiments, the proteases include, but are not limited to: peptidases, such as aminopeptidases, carboxypeptidases, and endopeptidases (e.g., trypsin, chymotrypsin, thermolysin, endoproteinase Lys C, endoproteinase GluC, endoproteinase ArgC, endoproteinase AspN). Aminopeptidases and carboxypeptidases are useful in characterizing post-translational modifications and processing events. Combinations of proteases also can be used. In one embodiment, the proteases and/or other enzymes can be immobilized onto the microchannel surface using adsorptive or covalent methods. In some embodiments, examples of covalent immobilization include direct covalent attachment of the protease to a surface with ligands such as glutaraldehyde, isothiocyanate, and cyanogen bromide. In other embodiments, the proteases may be attached using binding partners which specifically react with the proteases or which bind to or react with molecules which are themselves coupled to the proteases (e.g., covalently). Binding pairs may include the following: cytostatin/papain, valphosphanate/carboxypeptidase A, biotin/streptavidin, riboflavin/riboflavin binding protein, antigen/antibody binding pairs, or combinations thereof.

In one embodiment, the steps of concentrating polypeptides obtained from a given cell, producing digestion products, and analyzing digestion products to determine protein sequence, can be performed in parallel and/or iteratively for a given sample, providing a proteome map of the cell from which the polypeptides were obtained. Proteome maps from multiple different cells can be compared to identify differentially expressed polypeptides in these cells, and in other embodiments, the cells may be subjected to various treatments, conditions, or extracted from various sources, with the proteome map thus generated reflecting differential protein expression as a result of the status of the cell. It is to be understood that such concentration and assay comprise methods of this invention.

In some embodiments, the devices/methods of this invention may be used to concentrate a desired material from a biological sample. In some embodiments, the biological sample may be a fluid. In one embodiment, such a fluid may comprise bodily fluids such as, in some embodiments, blood, urine, serum, lymph, saliva, anal and vaginal secretions, perspiration and semen, or in another embodiment, homogenates of solid tissues, as described, such as, for example, liver, spleen, bone marrow, lung, muscle, nervous system tissue, etc., and may be obtained from virtually any organism, including, for example mammals, rodents, bacteria, etc. In some embodiments, the solutions or buffered media may comprise environmental samples such as, for example, materials obtained from air, agricultural, water or soil sources, which are present in a fluid which can be subjected to the methods of this invention. In another embodiment, such samples may be biological warfare agent samples; research samples and may comprise, for example, glycoproteins, biotoxins, purified proteins, etc. In another embodiment, such fluids may be diluted.

In one embodiment, this invention provides an array architecture that is capable of being scaled to at least 10,000 concentrators, suitable for a real-world screen.

In one embodiment, concentration efficiency may be determined by using labeled proteins or polypeptides, introduced into the concentrator in known ratios and detecting the concentrated labeled protein or polypeptides, such as exemplified herein below. Signal intensity can be determined as a function of time, over background noise.

In one embodiment, the concentrators of this invention may be under controlled physicochemical parameters, which may comprise temperature, pH, salt concentration, or a combination thereof.

In one embodiment, the invention provides for a method of concentrating a species of interest in a liquid, comprising using a device of the invention, or one prepared by a process as herein described.

In one embodiment, the invention provides for a method of concentrating a species of interest in a liquid, the method comprising applying a liquid comprising the species of interest a device of this invention, the device comprising:
  a fluidic chip comprising a planar array of channels through which a liquid comprising a species of interest can be made to pass;
  at least one rigid substrate connected thereto such that at least a portion of a surface of said substrate bounds said channels; and
  a high aspect ratio ion-selective membrane embedded within said chip, attached to at least a portion of said channels.

In one embodiment, the method further comprises the steps of:
  inducing an electric field in the channel whereby ion depletion occurs in a region in the channel proximal to the high aspect ratio ion-selective membrane, and a space charge layer is formed within the channel, which provides an energy barrier to the species of interest; and
  inducing liquid flow in the channel.

In one embodiment, the flow is electroosmotic, or in another embodiment, the flow is pressure driven.

In one embodiment, the steps are carried out cyclically.

In one embodiment, inducing an electric field in said channel is by applying voltage to said device, which in one embodiment is between 50 mV and 1500 V. In one embodiment, equal voltage is applied to the two sides of the channel, or in another embodiment, greater voltage is applied to the anodic side of the channel, as compared to the cathodic side.

In one embodiment, a space charge layer is generated in the channel prior to applying greater voltage to the anodic side of said channel.

According to this aspect of the invention and in another embodiment, the device is coupled to a separation system, detection system, analysis system or combination thereof.

In one embodiment, the liquid is a solution. In another embodiment, the liquid is a suspension, which, in another embodiment is an organ homogenate, cell extract or blood sample. In one embodiment, the species of interest comprises proteins, polypeptides, nucleic acids, viral particles, or combinations thereof. In one embodiment, the species of interest is a protein, nucleic acid, virus or viral particle found in, or secreted from a cell, and in another embodiment, is found in very low quantities, such that it represents less than 10% of the protein extracted form a protein extract of the cell.

In one embodiment, the methods of this invention and the devices of this invention enable collection of molecules from a relatively large (~1 μL or larger) sample volume, and their concentration into a small (1 pL~1 nL) volume. Such concentrated sample can then, in other embodiments, be efficiently sorted, separated or detected by various microfluidic systems, without sacrificing the overall detection sensitivity caused by the small sample volume capacity of microfluidic biomolecule sorting/detection systems. In other embodiments the volume of the concentrated species is large (~10 nL).

In one embodiment, the methods and concentrating devices of this invention allow for significantly increased signal intensity of a molecules, and subsequent just detection, which, in another embodiment, allows for more aggressive molecular sorting and/or removal of high-abundance molecules, such as proteins, from a sample, without sacrificing the detectability of molecules in minute concentration, such as minor proteins or peptides.

In another embodiment, the devices for and methods of concentration of this invention enable the use of several non-labeling detection techniques (UV absorption, for example), which was not possible due to the short path length and small internal volume of conventional microfluidic channels. Therefore, in another embodiment, the devices for and methods of concentration of this invention, which combine concentration and molecular sorting may provide an ideal platform for integrated Microsystems for biomarker detection, environmental analysis, and chemical-biological agent detection.

In one embodiment, the method further comprises the step of releasing the species of interest from the device. In one embodiment, the method further comprises the step of subjecting the species of interest to capillary electrophoresis.

Capillary electrophoresis is a technique that utilizes the electrophoretic nature of molecules and/or the electroosmotic flow of samples in small capillary tubes to separate sample components. Typically a fused silica capillary of 100 μm inner diameter or less is filled with a buffer solution containing an electrolyte. Each end of the capillary is placed in a separate fluidic reservoir containing a buffer electrolyte. A potential voltage is placed in one of the buffer reservoirs and a second potential voltage is placed in the other buffer reservoir. Positively and negatively charged species will migrate in opposite directions through the capillary under the influence of the electric field established by the two potential voltages applied to the buffer reservoirs. The electroosmotic flow and the electrophoretic mobility of each component of a fluid will determine the overall migration for each fluidic component. The fluid flow profile resulting from electroosmotic flow is flat due to the reduction in frictional drag along the walls of the separation channel. The observed mobility is the sum of the electroosmotic and electrophoretic mobilities, and the observed velocity is the sum of the electroosmotic and electrophoretic velocities.

In one embodiment of the invention, a capillary electrophoresis system is micromachined onto a device, which is a part of, or separate from, the concentrating device described herein. Methods of micromachining capillary electrophoresis systems onto devices are well known in the art and are described, for example in U.S. Pat. Nos. 6,274,089; 6,271,021; Effenhauser et al., 1993, Anal. Chem. 65: 2637-2642; Harrison et al., 1993, Science 261: 895-897; Jacobson et al., 1994, Anal. Chem. 66:1107-1113; and Jacobson et al., 1994, Anal. Chem. 66: 1114-1118.

In one embodiment, the capillary electrophoresis separations provide a sample which may then be used for both MALDI-MS and/or ESI-MS/MS-based protein analyses (see, e.g., Feng et al., 2000, Journal of the American Society For Mass Spectrometry 11: 94-99; Koziel, New Orleans, La. 2000; Khandurina et al., 1999, Analytical Chemistry 71: 1815-1819.

In other embodiments, downstream separation devices, which may interface with the concentrator of this invention include, but are not limited to, micro high performance liquid chromatographic columns, for example, reverse-phase, ion-exchange, and affinity columns.

It is to be understood that the exact configuration of any systems, devices, etc. which are coupled downstream of the concentrating device are to be considered as part of this invention, and that the configuration may be varied, to suit a desired application. In one embodiment, a module for separation of the concentrated peptides which is positioned downstream of the concentrating device comprises a separation medium and a capillary between the ends of which an electric field is applied. The transport of a separation medium in the capillary system and the injection of the sample to be tested (e.g., a sample band comprising peptides and/or partially digested polypeptides) into the separation medium can be carried out with the aid of pumps and valves, or in another embodiment, via electric fields applied to various points of the capillary.

In another embodiment, the method is utilized to detect said species of interest when said species is present in said liquid at a concentration, which is below a limit of detection.

In some embodiments concentration and assay of low abundance proteins is readily accomplished with the devices/methods of this invention. Concentration of a low abundance protein of $10^4$ times was achieved in as little as 4 minutes, and a roughly 1000-fold enhancement in assay sensitivity was achieved, as compared to similar assay without using the concentration methods/devices of this invention.

In other embodiments, various applications of the methods of the present invention are possible without deviating from the present invention.

By way of example, the concentrating and pumping methods of the present invention allow for high-throughput robotic assaying systems to directly interface with the devices of the present invention, and to concentrate a species of interest, and/or and pump liquid.

Various modes of carrying out the invention are contemplated as being within the scope of the following claims particularly pointing out and distinctly claiming the subject matter, which is regarded as the invention.

EXAMPLES

Materials and Methods

Device Fabrication:

Fabrication techniques for a microfluidic device comprising micro- or nano-channels were similar to those described (J. Han, H. G. Craighead, *J. Vac. Sci. Technol., A* 17, 2142-2147 (1999); J. Han, H. G. Craighead, *Science* 288, 1026-1029 (2000)). A PDMS device comprising microchannels was fabricated.

A Nafion perfluorinated resin solution (5 wt. % in lower aliphatic alcohols and water containing 15-20% water) was used to form a high aspect ratio Nafion membrane embedded within the PDMS chip. The membrane was cured and integrated into the chip. The cover glass was adhered to the chip by plasma bonding the PDMS chip containing the channels on top of the glass substrate.

An embodiment of a detailed scheme of the preparation of a device of this invention was carried out as follows: desired PDMS microchannels were obtained from a standard PDMS chip fabrication process. Microchannels with various dimensions were fabricated. Dimensions of channels fabricated were 50 micron width×5 micron depth, 100 micron width×10 micron depth, 1000 micron width×100 micron depth. The center microchannel was connected to side channels through one side wall in a single gate (SG) device and through both side walls in a double gate (DG) device. A mechanical cut was made across the microchannels using a conventional razor blade for guiding Nafion infiltration after punching sample loading holes. The depth of the cutting was large enough to reach over the microchannel depth. The depth of the cut was typically 500-1000 micron. Once the gap was created, PDMS tended to restore its inherent geometric structure due to its flexibility. By bending the chip, the gap was opened and a drop of 1.5 µL Nafion 117 solution (Fluka) was applied to the edge of the gap. The Nafion solution immediately filled the both the gap and a portion of the microchannels by capillary forces. Nafion is a sulfonated tetrafluorethylene copolymer, widely used as a proton conductor for proton exchange membranes. After 10 minutes of curing at 95° c, solvents in the Nafion resin evaporated, and the gap was bonded by Nafion resin with the adhesive-assisting role of the Nafion resin. The elastic nature of PDMS seals the Nafion junction rather tightly between the PDMS walls in the gap. Any remaining Nafion resin on the top of the PDMS surface and in the channels was removed by taping and peeling, and vertical type junctions were created within the PDMS, proximal to the microchannel bottom and proximal to the microchannel walls. Finally, a glass plate was bonded on top of the device using plasma treatment.

Biomolecule and Reagent Preparation

Figure 1A:
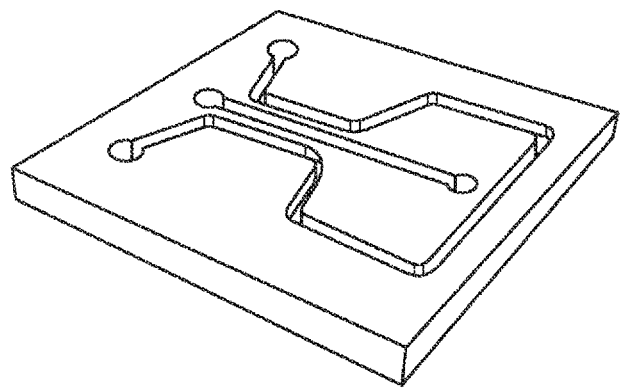
FIG. 1 schematically depicts embodiments of methods for fabricating the devices of the invention; PDMS microchannels are obtained from the standard chip fabrication process (FIG. 1a); a razor blade is used to cut across the microchannels for guiding Nafion infiltration after punching sample loading holes (FIG. 1b); the depth of the cutting reaches below the microchannel depth; by bending the chip, the gap was opened and a drop of 1.5 µL Nafion 117 solution (Fluka) was loaded into the loading holes (FIG. 1c); The Nafion solution immediately fill both the gap and a portion of the microchannels by capillary forces; After 10 minutes of curing at 95° c, solvents in the Nafion resin evaporate and the gap is bonded by the Nafion resin (FIG. 1d); the elastic nature of the PDMS facilitates tight sealing of the Nafion in the gap; any remaining Nafion on the top of the PDMS surface is removed by taping and peeling, and vertical or planar type junctions are formed (inserts in FIG. 1d); a glass plate is bonded on top of the device using plasma treatment (FIG. 1e).
Figure 1B:
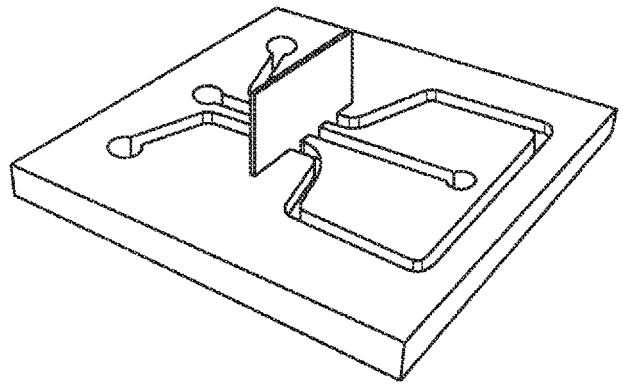
Figure 1C:
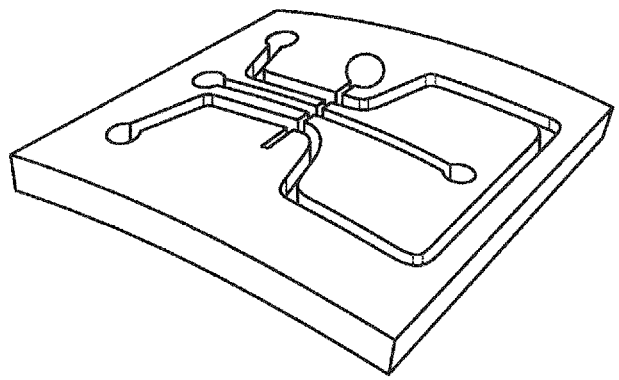
Figure 1D:
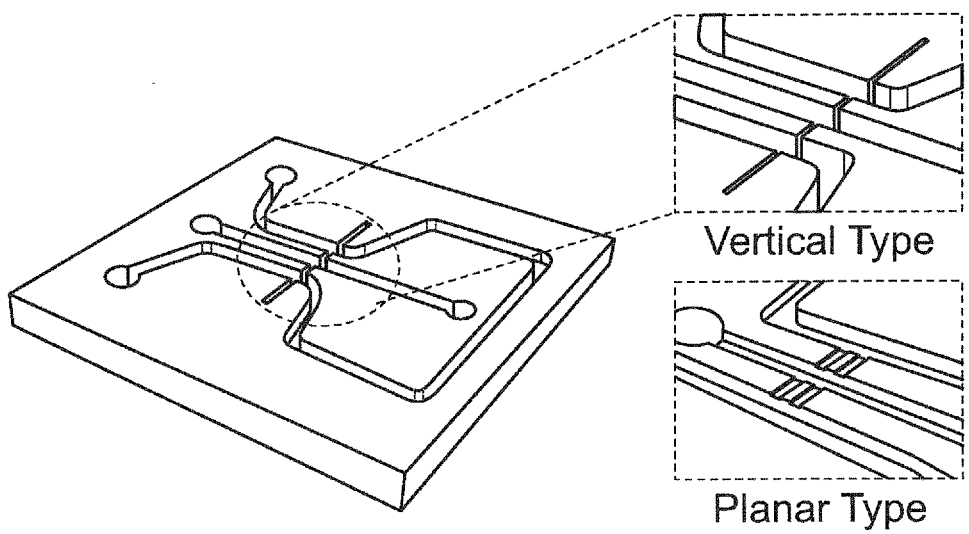
Figure 1E:
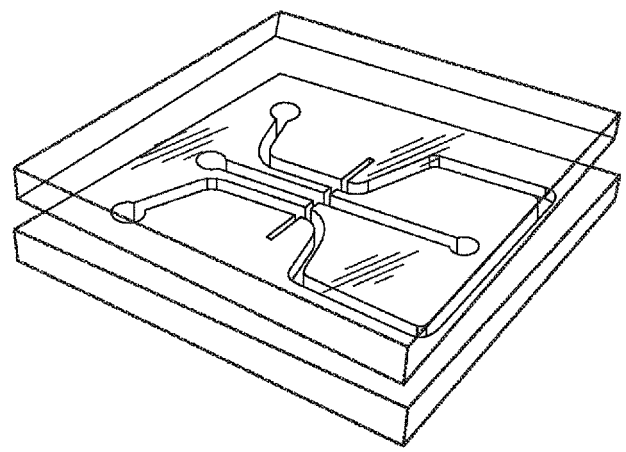
Figure 2A:
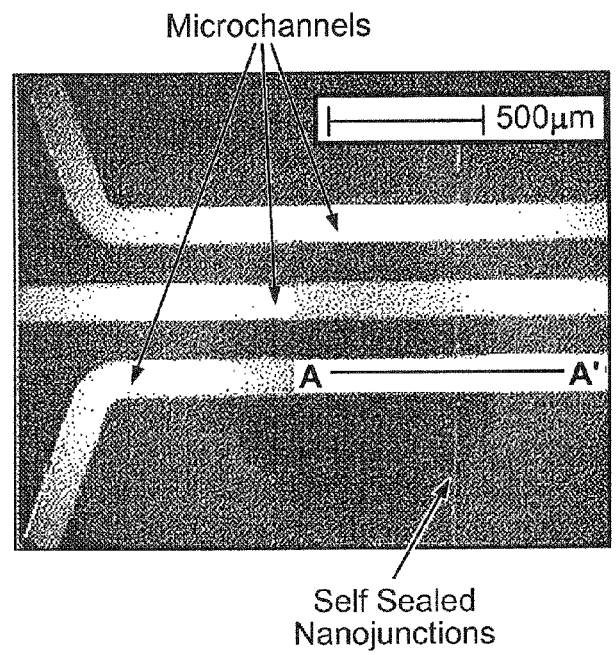
FIG. 2 shows scanning electron microscope (SEM) images of a device of this invention. Three microchannels were connected to each other by self-sealing Nafion membrane structure (FIG. 2a)
FIG. 2b is the SEM image of a cross section (A-A' in FIG. 2a) of the membrane. Nafion resin was filled perpendicular to the plane of the cover glass and the Nafion membrane thickness was estimated to be ~2-4 µm (FIG. 2b insert)
FIG. 2c is a current/voltage (I/V) plot for confirming repeatability. The ion current through the Nafion membrane was measured as a function of voltage applied.
Figure 2B:
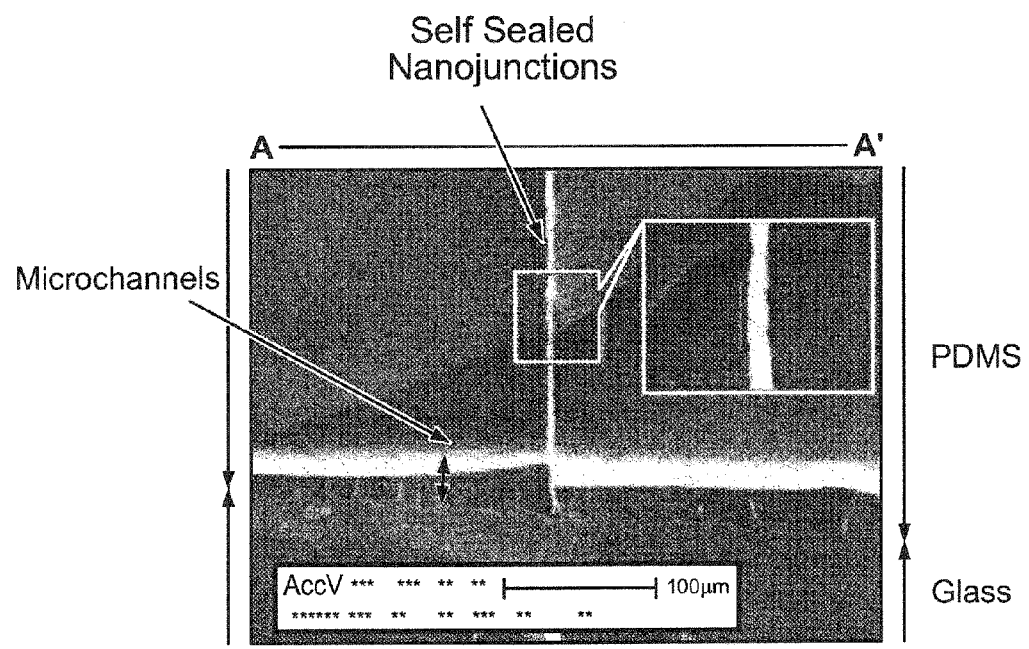
Figure 2C:
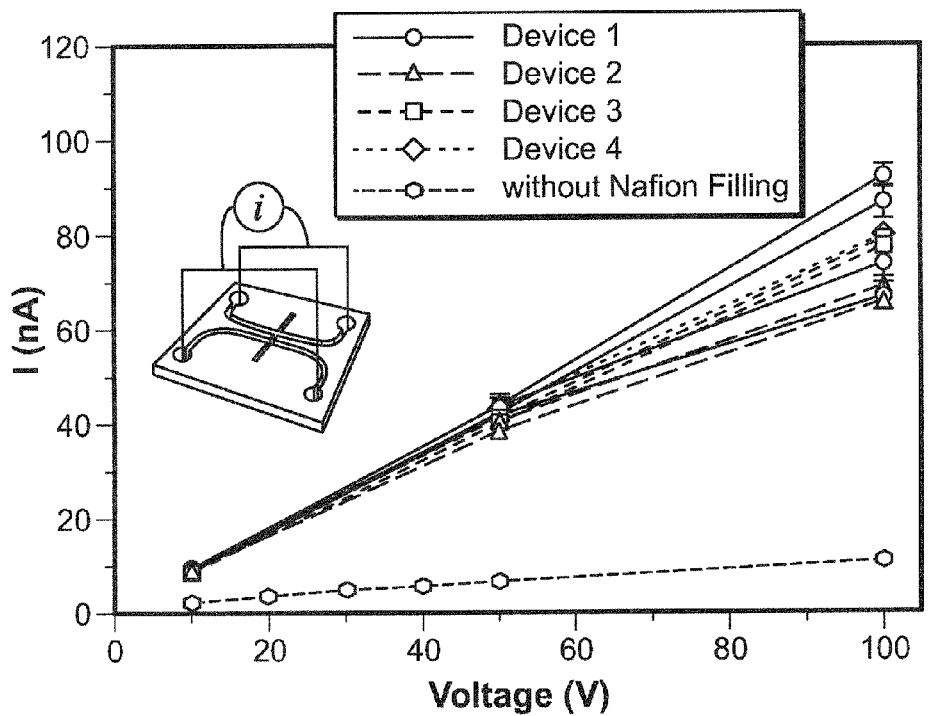

Molecules and dyes used included B-phycoerythrin, rGFP (BD bioscience, Palo Alto, Calif.), HTC-BSA (Sigma-Aldrich, St. Louis, Mo.), FITC-Ovalbumin (Molecular Probes, Eugene, Oreg.), HTC-BSA (Sigma-Aldrich, St. Louis, Mo.), HTC dye (Sigma-Aldrich, St. Louis, Mo.), Mito Orange (Molecular Probes, Eugene, Oreg.), and lambda-DNA (500 µg/ml). DNA molecules were labeled with YOYO-1 intercalating dyes (Molecular Probles, Eugene, Oreg.) by following manufacturer's instruction Scanning Electron Microscopy of Devices The microscope image of fabricated junctions and of the microchannels of DG devices were taken and are shown in FIG. 2. The images show three microchannels that were connected to each other by the high aspect ratio ion selective membrane which was assembled across the microchannels. FIG. 2b is an SEM image showing an image of a cross section (A-A') of the device. Nafion resin was filled perpendicular to the plane of the cover glass and its thickness was estimated to be about 2-4 microns, as shown in the magnified image. Since the Nafion resin reached over 100 microns in depth, it can be used as a "vertical type junction". Voids in the junction that could lead to unwanted leakage along the junction could not be seen. This vertical type Nafion junction had the dimensions of ~1000 micron depth×~1 micron width. The cross sectional area of the formed junctions which is critical for high currents is theoretically at least $1\times10^4$ times larger than in the case of low aspect ratio or planar membranes.

Repeatability Test

The DC ion current through the polymeric junction is an indicator for testing reliability and repeatability of the performance of devices of the present invention. The initial ion currents were measured and compared for different devices. The measurement was done using Keithley 236 Current/Voltage Source-Measure Unit (Keithley Instruments, Inc.) which was connected to the SG device with microchannels dimensions of 50 micron width×5 micron depth. In order to control the level of electrical double layer overlapping, 1 mM phosphate buffer was used. Four devices were fabricated and tested. Each device was tested three times. The current was proportional to the applied voltage and showed an excellent linearity when the applied voltage was under 50 V. For most applications the voltage does not exceed this limit. The results demonstrate the reliability and reproducibility of the fabrication method and of the devices. The devices measured were compared to a device lacking the Nafion membrane. In this device the current was less than 10 nA which was not sufficient to induce ion concentration polarization (ion depletion).

Optical Detection Setup

All the experiments were conducted on an inverted microscope (IX-51) with fluorescence excitation light source attached. A thermoelectrically cooled CCD camera (Cooke Co., Auburn Hill, Mich.) was used for fluorescence imaging. Sequences of images were analyzed by IPLab 3.6 (Scanalytics, Fairfax, Va.). A home-made voltage divider was used to distribute different potentials to reservoirs. The built in 100 W mercury lamp was used as a light source.

Channels were filled with 40 nM, 4 nM and 4 μM B-phycoerythrin solutions, and the fluorescence intensity was determined. The camera shutter was opened only during periodical exposures (~1 sec) to minimize photobleaching of the collected molecules.

Example 1

Ion/Protein Concentration

Figure 3A:
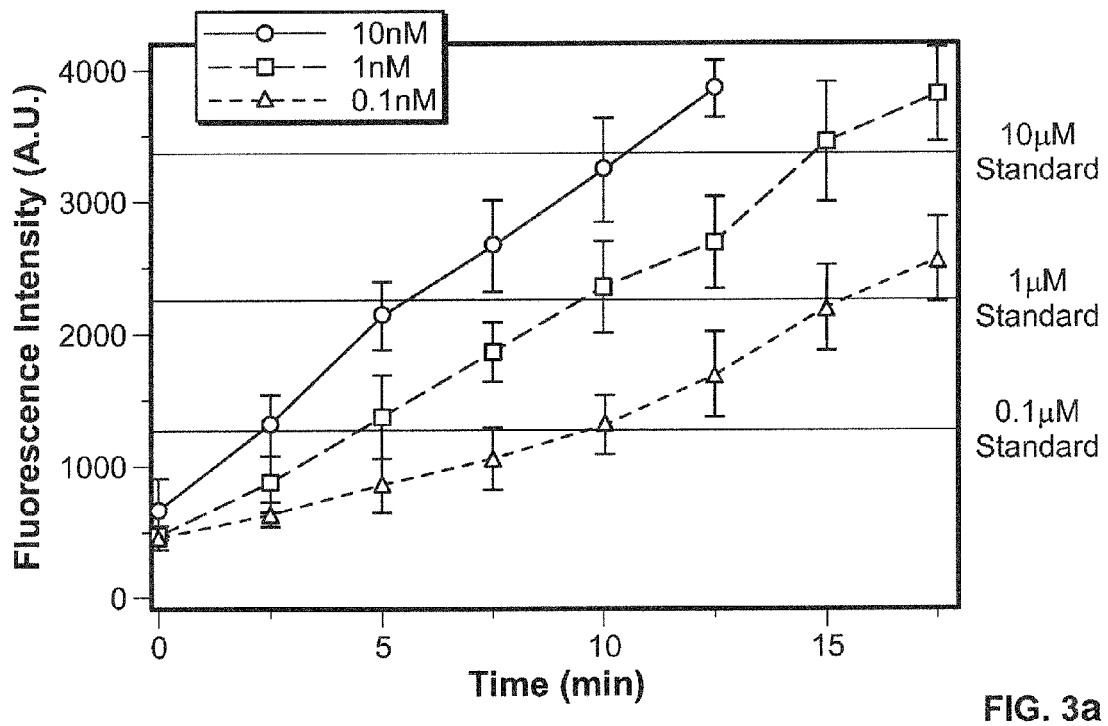
FIG. 3a shows the preconcentration factors of BODIPY disulfonate (Invitrogen) for three different concentrations (0.1 nM, 1 nM and 10 nM) in 1 mM phosphate buffer solution using a double gate (DG) device. The fluorescent intensities were measured and analyzed with an inverted fluorescence microscope (IX-51) with a CCD camera (SensiCam, Cooke corp.) and Image Pro Plus 5.0 (Media Cybernetics inc.). Results show that preconcentration factors of up to $1\times10^4$ are achieved within 15 minutes. The concentration factors depend on the operating conditions such as applied voltage, charges of species, buffer concentrations and microchannel dimensions. The preconcentration of β-phycoerythrin (β-PE) protein in the device is shown in FIG. 3b for two initial concentrations of 1.67 nM and 16.7 pM. Concentration factors of up to $1\times10^4$ were achieved within 22 minutes.
Figure 3B:
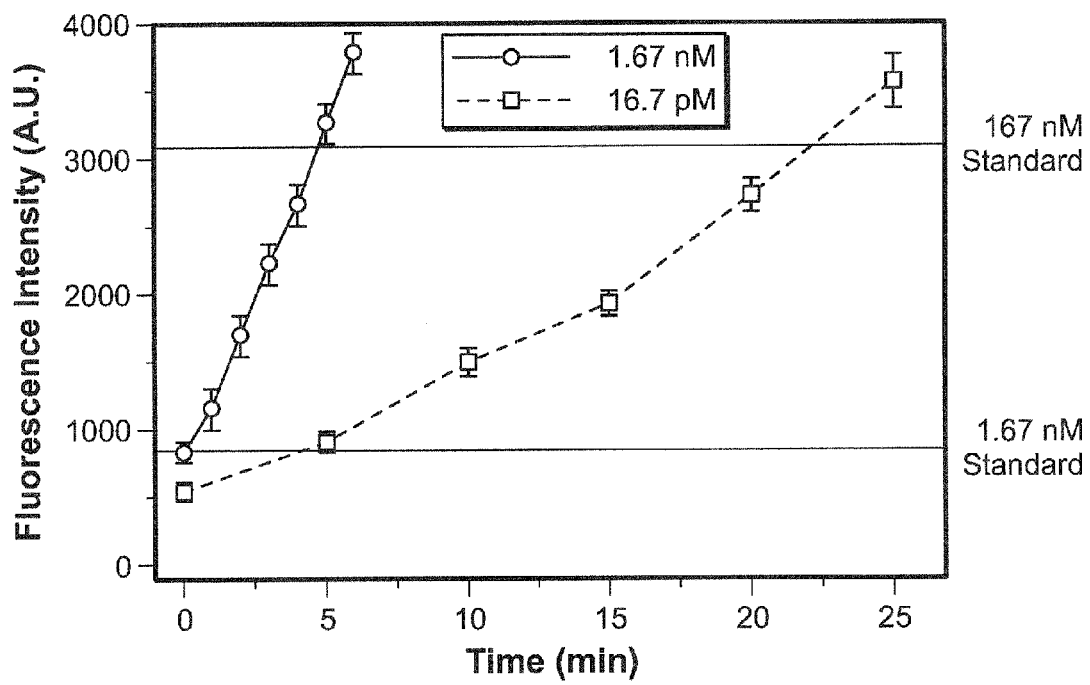
FIG. 3 depicts an embodiment of a preconcentration test in a device of the present invention.

The preconcentration factors of BODIPY disulfonate (Invitrogen) were measured using a device and methods of this invention. Three different solution concentrations were used. The concentrations used were 0.1 nM, 1 nM and 10 nM, in a 1 mM phosphate buffer solution. A DG device was used. Microchannels had dimensions of 100 microns width×10 micron depth as shown in FIG. 3a. The average tangential electric field was 50 V/cm. The fluorescent intensities were measured and analyzed as described in the method section herein above. Compared with its standard signal intensities (0.1 μM, 1 μM and 10 μM) the results showed that preconcentration factors of up to $1 \times 10^4$ were achieved within 15 minutes. The preconcentration of β-phycoerythrin (β-PE) protein in the same device was measured. The preconcentration for two initial concentrations (1.67 nM and 16.7 pM) was measured and is shown in FIG. 3b. The $1 \times 10^4$ preconcentration factors were achieved after 22 minutes. It was concluded that the concentration factors largely depend on the operating conditions such as applied voltage, charges of target species, buffer concentrations and the dimensions of the microchannel.

Example 2

Pressure Driven Ion/Protein Preconcentration Operation

Figure 4:
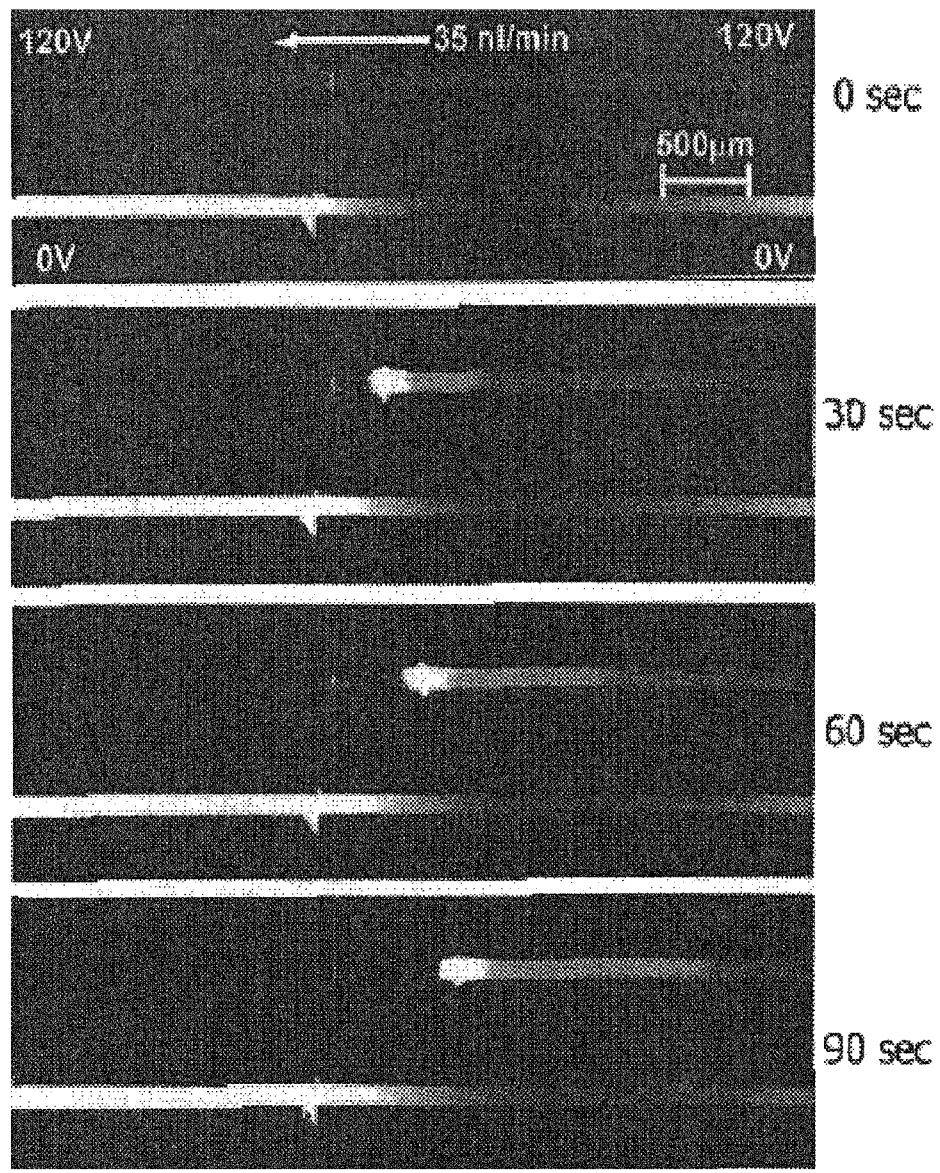
FIG. 4 depicts an embodiment of the mechanism of concentration of charged species in a device of this invention using external pressure fields. An operation voltage of 120 V was applied at both reservoirs and the external pressure flow was induced by a syringe pump (Harvard) at 35 nL/min. The preconcentration speed (seven minutes) was doubled when compared to the speed when no external pressure was applied (15 minutes).

Pressure driven preconcentration operations were conducted in devices of the present invention. FIG. 4 shows the preconcentration operation using external pressure fields. Operation voltages of 120 V were applied at both reservoirs causing a depletion voltage condition. External pressure flow was induced by a syringe pump (Harvard) at 35 nL/min from right to left. This tangential pressure flow (35 nL/min corresponding to 2.6 mm/sec in linear fluid velocity in this microchannel dimension) was at least 20 times faster than the electrokinetic velocity that can be obtained by the tangential field of 50 V/cm used in FIG. 3. The speed of preconcentration was enhanced approximately 2× compared to the speed shown in FIG. 3. The preconcentration reached $1 \times 10^4$ within 7 minutes in FIG. 4.

Example 3

High Performance Nanofluidic Pumping

Figure 5A:
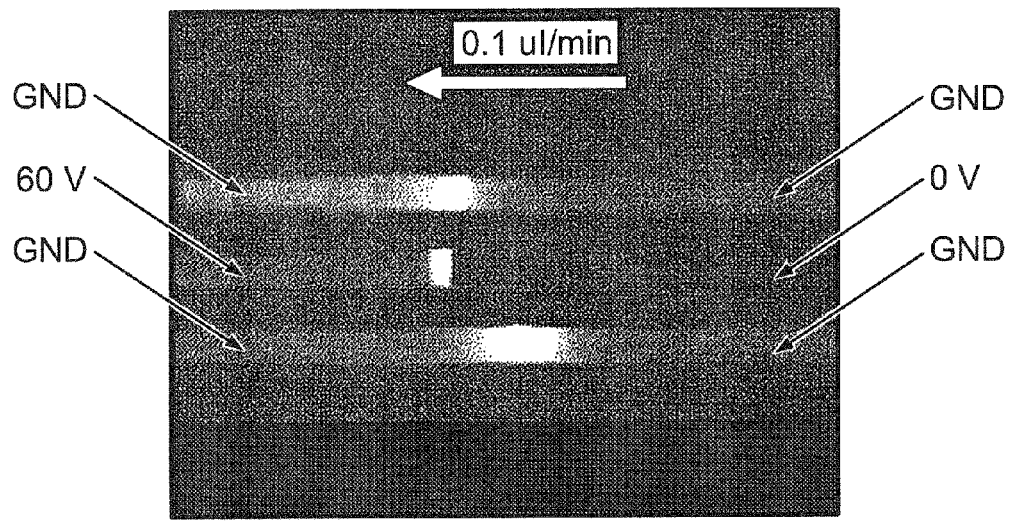
FIG. 5 depicts one embodiment of the pre-concentrator operating scheme high performance nanofluidic pumping. Low concentrations of ions near the depletion zone result in a very high electric fields (up to ~kV/cm). Thus, the flow inside the zone can push the sample liquid along the microchannel. This flow can reverse the pressure flow as seen in FIG. 5a. The graph in FIG. 5b. show the flow reverse process. Voltage was increased at a rate of 50 V/30 sec up to 300 V. The mechanism shown can be used as a pump and can also be used for flow switching and gating.
Figure 5B:
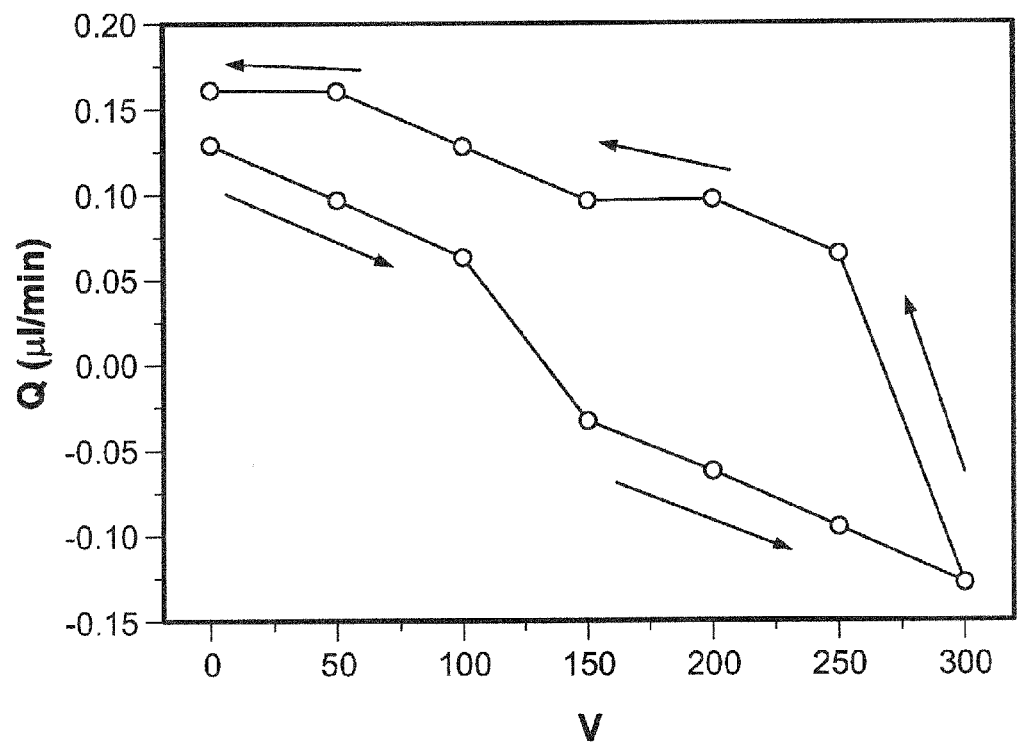

The ionic concentration inside the ion depletion zone created near the membrane junction is so low that the solution can be considered desalted (below a few μM). In such a case the electric field inside this zone increases up to ~kV/cm, even when an external electric field of 10 V/cm was applied. Thus the flow inside the zone experienced extremely high electric field and pushed the sample liquid all along the microchannel. This flow has reversed the pressure flow from opposite reservoir as shown in FIG. 5a. A syringe pump was connected to the right center reservoir with 0.1 μL/min flow. Initially, all liquid flew from right to left without external electric field. While keeping the 0 V at the right center reservoir, increasing the voltage at the left center reservoir initiated a concentration polarization near the membrane. After a certain voltage (60 V) was reached, the ion depletion zone was successfully created at the left hand side of the junction and it acted as a high performance pump. This operation can push the flow against the external pressure field as shown in FIG. 5b.

Example 4

Ion Depletion and Preconcentration in a Semi Macro Channel

Figure 6A:
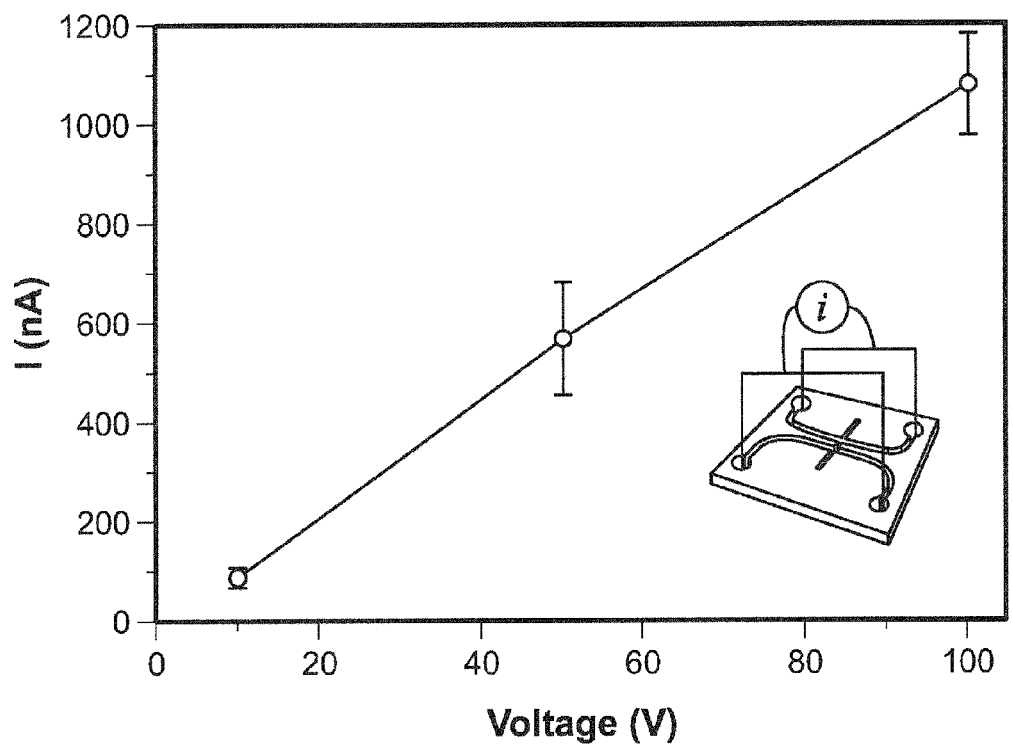
FIG. 6 is a plot of depicts one embodiment of the pre-concentrator operating scheme for a semi-macrochannel. A large macrochannel with the dimensions of 1000 µm (width)× 100 µm (depth) was fabricated. Ion currents through the Nafion membrane were approximately 10 times higher than ion currents in a channel with the dimensions of 100 µm (width)×10 µm (depth) (compare FIG. 2c to FIG. 6a). Ion depletion in a single gate (SG) device is shown in FIG. 6b. Ion preconcentration in a DG device is shown in FIG. 6c. The volume of the preconcentration plug was nearly 10 nL which has never been demonstrated before. This device is suitable for connection to commercial analytical systems such as mass spectrometry (MS) and matrix-assisted laser desorption/ionization (MALDI).
Figure 6B:
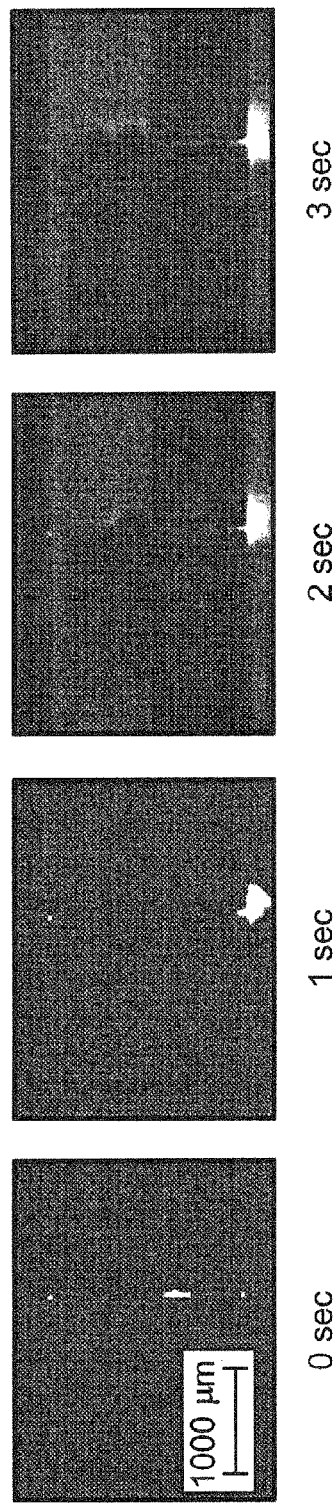
Figure 6C:
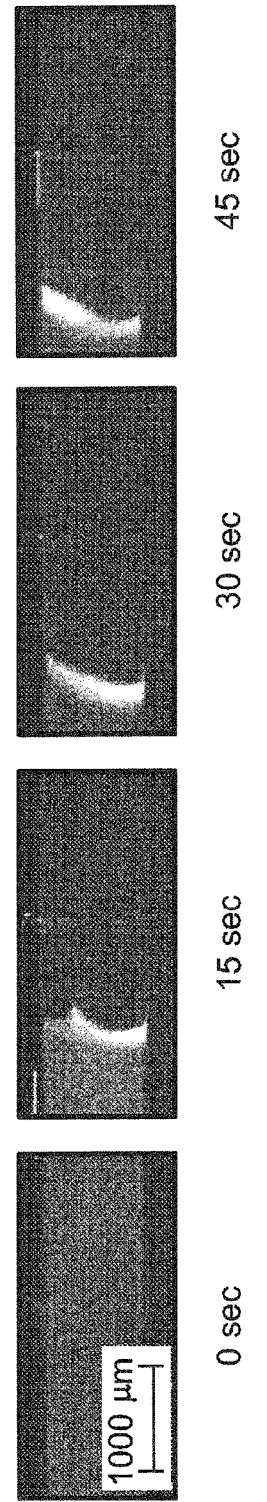

In order to demonstrate the efficiency of the high aspect ratio ion selective membrane devices, a larger microchannel was fabricated. The channel dimensions were 1000 μm width×100 μm depth. Since the deeper microchannel gives higher ion current, in the high aspect ratio configuration ion current through the membrane was approximately 10 times larger than in the smaller (100 μm width×10 μm depth) channel. This is shown in FIG. 6a and is compared with FIG. 2c. Due to this high ion current through the ion selective membrane, ion depletion was demonstrated in an SG device as shown in FIG. 6b, and ion preconcentration in a DG device as shown in FIG. 6c. The volume of the preconcentration plug was nearly 10 nL which was never demonstrated before and is suitable for applications in which the device is connected to commercial analytical systems such as mass spectrometers and matrix assisted laser desorption/ionization (MALDI) instruments.

It will be understood by those skilled in the art that various changes in form and details may be made therein without departing from the spirit and scope of the invention as set forth in the appended claims. Those skilled in the art will recognize, or be able to ascertain using no more than routine experimentation, many equivalents to the specific embodiments of the invention described herein. Such equivalents are intended to be encompassed in the scope of the claims.

In the claims articles such as "a,", "an" and "the" mean one or more than one unless indicated to the contrary or otherwise evident from the context. Claims or descriptions that include "or" or "and/or" between members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides, in various embodiments, all variations, combinations, and permutations in which one or more limitations, elements, clauses, descriptive terms, etc., from one or more of the listed claims is introduced into another claim dependent on the same base claim unless otherwise indicated or unless it would be evident to one of ordinary skill in the art that a contradiction or inconsistency would arise. Where elements are presented as lists, e.g., in Markush group format or the like, it is to be understood that each subgroup of the elements is also disclosed, and any element(s) can be removed from the group.

It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in haec verba herein.

Certain claims are presented in dependent form for the sake of convenience, but Applicant reserves the right to rewrite any dependent claim in independent format to include the elements or limitations of the independent claim and any other claim(s) on which such claim depends, and such rewritten claim is to be considered equivalent in all respects to the dependent claim in whatever form it is in (either amended or unamended) prior to being rewritten in independent format.

What is claimed is:

1. A concentrating device comprising:
   a fluidic chip comprising a planar array of channels through which a liquid comprising a species of interest can be made to pass;
   at least one rigid substrate connected thereto such that at least a portion of a surface of said substrate bounds said channels;
   a high aspect ratio ion-selective membrane, embedded within said chip, attached to at least a portion of said channels, said membrane being formed by introducing said liquid to a portion in said chip;
   a unit to induce an electric field in said channels; and
   a unit to induce an electrokinetic or pressure driven flow in said channels.

2. The device of claim 1, wherein said unit to induce an electric field in said channel is a voltage supply.

3. The device of claim 2, wherein a voltage applied by said voltage supply is between 50 mV and 1500 V.

4. The device of claim 2, wherein said voltage supply applies equal voltage to opposing sides of said channel.

5. The device of claim 2, wherein said voltage supply applies greater voltage to an anodic side of said channel, as compared to a cathodic side of said channel.

6. The device of claim 1, wherein a width of said channel is between 0.1-500 μm.

7. The device of claim 1, wherein a depth of said channel is between 5-50 μm.

8. The device of claim 1, wherein a depth of said channel is between 50-150 μm.

9. The device of claim 1, wherein said rigid substrate comprises pyrex, silicon, silicon dioxide, silicon nitride, quartz, PMMA, PC or acryl.

10. The device of claim 1, wherein said fluidic chip comprises polydimethylsiloxane.

11. The device of claim 1, wherein said high aspect ratio ion-selective membrane comprises polytetrafluoroethylenes (PTFEs), polyphosphazenes, polybenzimidazoles (PBIs), poly-zirconia, polyethyleneimine- poly(acrylic acid), perfluorosulfonates, non-fluorinated hydrocarbon polymers, polymer-inorganic composites or poly(ethylene oxide).

12. The device of claim 1, wherein said liquid comprises sulfonated tetrafluorethylene copolymer.

13. The device of claim 12, wherein said sulfonated tetrafluoroethylene comprises a Nafion solution.

14. The device of claim 1, wherein said high aspect ratio membrane comprises microparticles or beads.

15. The device of claim 14, wherein said microparticles or beads comprising silica or polystyrene.

16. The device of claim 1, wherein said high aspect ratio ion-selective membrane has a width of 1-10 μm.

17. The device of claim 1, wherein said ion-selective membrane has a depth of 550-1050 μm.

18. The device of claim 1, wherein a surface of said channel has been functionalized to reduce or enhance adsorption of said species of interest to said surface.

19. The device of claim 1, wherein the surface of the channel has been functionalized to enhance or reduce the operation efficiency of the device.

20. The device of claim 1, wherein said high aspect ratio ion selective membrane is not in contact or is in minimal contact with said rigid substrate.

21. The device of claim 1, wherein said unit to induce an electric field in said channel comprises at least a pair of electrodes and a power supply.

22. The device of claim 1, wherein said device is coupled to a separation system, detection system, analysis system or combination thereof.

23. The device of claim 1, wherein the device is coupled to a mass spectrometer.

* * * * *